United States Patent [19]
Tam

[11] Patent Number: 5,580,563
[45] Date of Patent: Dec. 3, 1996

[54] MULTIPLE ANTIGEN PEPTIDE SYSTEM HAVING ADJUVANT PROPERTIES, VACCINES PREPARED THEREFROM AND METHODS OF USE THEREOF

[76] Inventor: James P. Tam, 607 S. Wilson Blvd., Nashville, Tenn. 37215

[21] Appl. No.: 331,489

[22] PCT Filed: May 3, 1993

[86] PCT No.: PCT/US93/04179

§ 371 Date: Dec. 28, 1994

§ 102(e) Date: Dec. 28, 1994

[87] PCT Pub. No.: WO93/22343

PCT Pub. Date: Nov. 11, 1993

Related U.S. Application Data

[63] Continuation-in-part of Ser. No. 877,613, May 1, 1992, abandoned.

[51] Int. Cl.$^6$ ............ A61K 39/39; A61K 39/385; A61K 9/127; A61K 39/02
[52] U.S. Cl. ............ 424/197.11; 424/193.1; 424/278.1; 424/DIG. 16; 424/450; 424/196.11; 424/194.1; 530/345; 530/403
[58] Field of Search ............ 424/196.11, 197.11, 424/201.1, 208.1, 450, 193.1, 194.11, 278.1, 283.1, DIG. 16; 530/325, 326, 365, 404, 405

[56] References Cited

PUBLICATIONS

Defoort et al (1992) in *Peptides Chemistry and Biology* Proceedings of the Twelfth American Peptide Symposium Jun. 16–21, 1991, Cambridge, Massachussets, USA, ed by J. A. Smith et al, ESCOM, Leiden, pp. 845–846.

Huang et al (1992) Ibid pp. 847–848.

Nardelli et al (1992) *Innovation and Perspectives in Solid Phase Synthesis,* Epton ed, Collected papers, Second International Symposium, 27th–31st. Aug., 1991, Canterbury, England, Intercept–Limited, Andrew, pp. 241–249.

Chem. Abstract. 118(13) 29 Mar. 1993 #125070j on p. 869 of Nardelli et al. (1992) *Innovation and Perspectives in Solid Phase Synthesis*, Epton ed. Collected pprs. 2nd Int. Symp. Aug. 27–31/1991, Canterbury, Engl; Intercept Limited, Andover pp. 241–249.

Defoort et al (1992) Proc. Natl. Acad. Sci. USA 89(9): 3879–83.

Defoort et al (1992) International J. Peptide and Protein Res. 80 (3/4) pp. 214–221.

Primary Examiner—Kay K. A. Kim
Attorney, Agent, or Firm—Klauber & Jackson

[57] ABSTRACT

A multiple antigenic peptide system is disclosed that comprises a dendritic core and peptide and a lipophilic anchoring moiety. This particular combination has as an advantage that it eliminates the need for the inclusion of adjuvants found to be toxic to humans, and facilitates the exponential amplification of the antigenic potential of a vaccine prepared therefrom, as noncovalent amplification by a liposome or micellar form is possible. Further, multiple different antigenic peptides may be attached so that the system may be prepared for administration to concurrently treat diverse ailments, such as for example, AIDS and influenza. The present multiple antigen peptide system is capable of eliciting an immune response when injected into a mammal, and accordingly, vaccines prepared from the system and methods of use including therapeutic protocols are included.

36 Claims, 12 Drawing Sheets

M

SM

MULTIPLE ANTIGEN PEPTIDE SYSTEM HAVING ADJUVANT PROPERTIES, VACCINES PREPARED THEREFROM AND METHODS OF USE THEREOF

The present invention was made with partial assistance from Grant No. AI28701. The Government may have certain rights in the invention.

CROSS-REFERENCE TO RELATED APPLICATIONS

This application is a continuation-in-part of application Ser. No. 07/877,613, filed May 1, 1992, which is now abandoned.

BACKGROUND OF THE INVENTION

The present invention relates generally to the field of immunology, and particularly to the preparation and administration of vaccines for prevention and treatment disease states such as HIV infection.

Highly specific and immunogenic antigens are preferred as vaccines. While the immunogenicity of an antigen can be increased by coupling a protein carrier to the antigen, this approach has several drawbacks. First, if the carrier is large, significant humoral immune response can be directed against the carrier rather than the antigen. Second, a large carrier can suppress humoral response to the antigen. Finally, the coupling of an antigen to a protein carrier can alter the immunogenic determinants of the antigen.

Multiple antigen peptide systems (MAPS) are designed to overcome the problems observed with conventional protein careers. Most MAPS are composed of several peptide antigens covalently linked to a branching, dendritic core composed of bifunctional units (e.g., lysines). Thus, a cluster of antigenic epitopes form the surface of a MAPS and a small matrix forms its core. As a result, the core is not immunogenic. MAPS have been used to prepare experimental vaccines against hepatitis (Tam et at., *Proc. Natl. Acad. Sci. USA* 86: 9084, 1989), malaria (Tam et at., *J. Exp. Med.* 171: 299, 1990), and foot-and-mouth disease. A further advantage of MAPS is that they are chemically unambiguous. This allows different epitopes, such as B cell and T cell epitopes, to be arranged in a particular arrangement and stoichiometry.

Specific MAPS have been and are in development for use in immunization against HIV. For example, European Patent Publication No. 0 339 695 published 11 Feb. 1989 describes a process for preparing MAPS by reacting a branched structure based on an amino acid such as lysine or ornithine with a separately synthesized antigenic compound.

European Patent Publication No. 0 328 403, published 16 Aug. 1989 describes particular peptides that are specifically immunoreactive with antibodies to HIV and suggests that MAPS which include these peptides can be used for immunization to prevent HIV infection.

Hart et al. (*J. Immunol.*, 145: 2677, 1990) report that a synthetic peptide construct which includes amino acids 428–443 and 303–321 of HIV-I-III, envelope protein gp120, when used as a carrier-free immunogen in primates, can induce a high titer of neutralizing anti-HIV antibodies and can induce T cell proliferative response against native HIV-1 gp120.

Palker et al. (*Immunology* 142: 3612, 1989) describes the use of a 16 amino acid T cell epitope from HIV-1-IIIB fused to a synthetic peptide which includes a type-specific neutralizing determinant of a particular HIV-1 strain (III. 1 MN or RF) to immunize goats. Both T cells and B cells responded to epitopes within the type-specific neutralizing determinant.

PCT Application Publication No. WO 90/11778 published 18 Oct. 1990 discloses multiple antigen peptide systems in which a large number of each of T cell and B cell malarial antigens are bound to the functional groups of a dendritic core molecule.

In Copending U.S. application Ser. No. 07/744,281, now abandoned, by Tam et al., a particular multiple antigen peptide is prepared for use as a vaccine for the treatment of HIV infection that incorporates particular peptides derived from the HIV-1 III$_B$ envelope protein as well as the V3 loop of the gp120 protein of HIV 1-MN. This peptide system demonstrates the capability of generating a humoral response and the development of antibodies, and seeks to elicit a T cell response by the inclusion of a T cell epitope. The in vivo administration of this peptide requires the inclusion of an adjuvant as a means of enhancing the humoral response.

More generally, most vaccine strategy developed today particularly against human immunodeficiency virus (HIV) infection has been directed toward the humoral response of generating neutralizing antibodies. Recent advances in mapping antigens involved in immune responses have allowed detailed characterization of epitopes that confer neutralizing, T-helper and T-cytotoxic responses. These developments have led to consideration of including the T-cytotoxic response along with humoral immunity in the design of peptide-based vaccines.

As noted above and elsewhere, traditional methods for preparing peptide vaccines that present peptides as macromolecules through conjugation to protein carriers or polymerization are often unable to induce cytotoxic T lymphocytes (CTL) response in vivo. Use of an adjuvant in the immunizing protocol has the advantage of enhancing the humoral response but has mixed results in priming specific CTL response. Furthermore, the most popular adjuvant used in laboratory animals, such as Freund's complete adjuvant, is too toxic and unacceptable for humans. Ideally, protection against viral infection is best provided by both humoral and cell-mediated immunities, including long-term memory and cytotoxic T cells.

Specifically, the human immunodeficiency virus (HIV), the etiologic agent of the acquired immunodeficiency syndrom (AIDS), has become an important objective for various vaccine developments. The predominant vaccine strategy has focused on the use of the envelope protein antigens gp120 and gp160 of HIV-1 produced by the recombinant DNA technology. However, the full promise of their use in vaccines will not be realized unless they are administered along with an effective adjuvant.

An adjuvant is usually a non-toxic agent that provokes specific responses to antigens. There is a wide spectrum of mechanisms by which an adjuvant functions. It can function by creating a depot at the site of injection that prolongs the release of antigens with antigen-presenting cells. It may also function by activating macrophages to release cytokines and mediators which in turn activate effector T cells or antibody-forming B cells. The net result is that an adjuvant augments specific humoral and cell-mediated immunities with a lower dose of antigen required.

Many seemingly unrelated agents have been used as adjuvants and the commonly used adjuvants can be broadly categorized into four groups. The first, and the only clinically acceptable group, belongs to the gels of aluminium (e.g. alum) and calcium salts. However, alum is a weak adjuvant and its formulation in laboratory tests of HIV and SIV antigens has been found to be inadequate. The second, and perhaps the most potent group, includes pure compounds and undefined mixtures derived from mycobacterial cell walls. Mixtures such as Freund's complete adjuvant (FCA) and lipopolysacchaxides (LPS) are the best known examples. However, FCA and LPS produce side effects. They are pyrogenic and induce arthritis in rats and anterior uveitis in rabbits.

A need therefore exists for the development of a vaccine formulation that offers improved immunity in both categories while avoiding the drawbacks of traditional adjuvant materials.

SUMMARY OF THE INVENTION

In accordance with the invention, a multiple antigenic peptide system is disclosed that comprises a dendritic core and at least one peptide and a lipophilic membrane anchoring moiety attached thereto, wherein the the multiple antigen peptide system, when injected into a mammal, is capable of eliciting a full immune response including both humoral and cytotoxic T cell responses.

More particularly, a synthetic peptide-based vaccine may be prepared from the present peptide antigen system, that is effective in providing both humoral and cell-mediated immunities, and is safe in its exclusion of Freund's complete adjuvant. The present invention employs a macromolecular assemblage principle that allows amplification of peptide antigens to a macromolecule. The resulting macromolecule bears the immunological mimicry of the external-surface coat protein of a pathogen.

The lipophilic anchoring moiety useful in the present invention may comprise a lipoamino acid, liposomes, saponin derivatives alone or in admixture with cholesterol, and suitable surfactant materials such as the PLURONICS comprising a mixture of long chain polyoxyethylenes and polyoxypropylenes. Particularly, a long side chain bearing amino acid such as tripalmitoyl-S-glyceryl cysteine (P3C) has been determined to be suitable. Analogs of P3C such as P2C and materials prepared from serine and lysine, the latter exemplified by palmitoyl lysine, as well as cysteine are likewise included herein.

The antigen system of the present invention is versatile, as the exponential magnification possible by the preparation of multiple antigens facilitates the presentation of multiple and different such antigens, so that immunization for several different and distinct infective stimuli is possible. For example, a single vaccine prepared in accordance herewith may present antigens for HIV, influenza and malaria, by the attachment to the core of coat proteins for each of these stimuli.

In a preferred embodiment, the multiple antigenic peptide system includes a T cell epitope. The T cell epitope may be covalently linked in tandem to the peptide. By "T cell epitope" is meant a peptide capable of eliciting a proliferative T cell response. Preferably, the T cell epitope is at least seven amino acids long.

In related aspect, the invention features a method for eliciting an immune response against HIV in a mammal. The method includes administering to the mammal the multiple antigen peptide system described above.

The invention further relates to a vaccine which includes an immunologically effective amount of the multiple antigen peptide system described above. The invention also extends to a method for generating antibodies by admininstering to a mammal an antibody-generating amount of the multiple antigen peptide system of the invention.

The scope and content of the invention will be better understood from a review of the detailed description which proceeds with reference to the following illustrative drawings.

DETAILED DESCRIPTION

Figure 1:
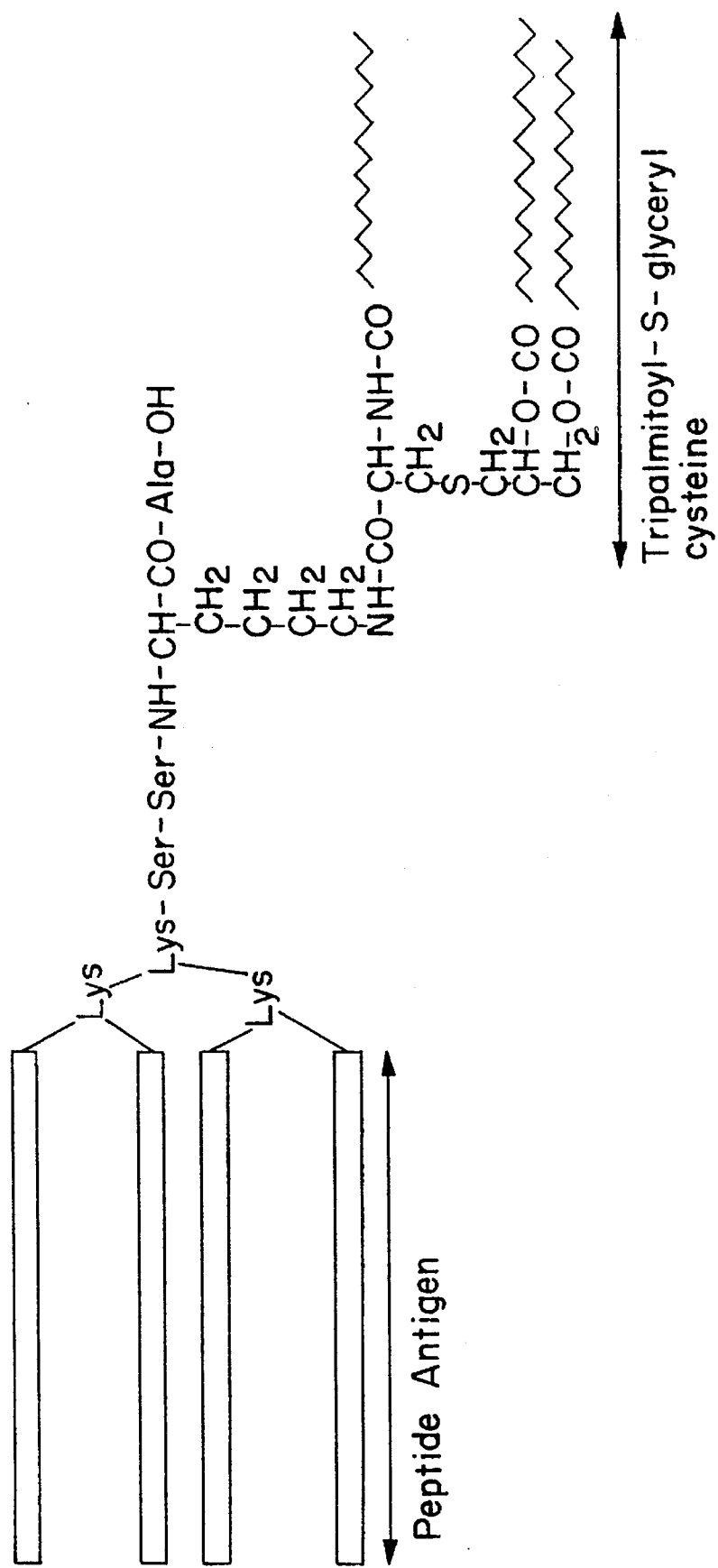
FIG. 1 is a schematic representation of MAP-P3C.

In its broadest aspect, the invention relates to multiple antigen peptide systems that include a lipophilic membrane anchoring moiety that confers adjuvant properties among its advantages. The dendritic core and the multiplicity of antigens attached thereto, however, are the characteristics of the antigenic materials that the present inventor and others have already developed. Accordingly, the following discussion is by way of background to the extent that the MAPS portion of the present system shares its origins with such previously prepared materials.

Multiple antigen peptide system (MAPS) is the commonly used name for a combination antigen/antigen carrier that is composed of two or more, usually identical, antigenic molecules covalently attached to a dendritic core which is composed of bifunctional units. The dendritic core of a multiple antigen peptide system can be composed of lysine molecules. For example, a lysine is attached via peptide bonds through each of its amino groups to two additional lysines. This second generation molecule has four free amino groups each of which can be covalently linked to an additional lysine to form a third generation molecule with eight free amino groups. A peptide may be attached to each of these free groups to form an octavalent multiple peptide antigen. Alternatively, the second generation molecule having four free amino groups can be used to form a tetravalent MAPS, i.e., a MAPS having four peptides covalently linked to the core. Many other molecules, including aspartic acid and glutamic acid, can be used to form the dendritic core of a multiple peptide antigen system. The dendritic core, and the entire MAPS may be conveniently synthesized on a solid resin using the classic Merrifield synthesis procedure.

Multiple antigen peptide systems have many advantages as antigen carrier systems. Their exact structure and composition is known; the ratio of antigen to carrier is quite high; and several different antigens, e.g., a B cell epitope and a T cell epitope, may be attached to a single dendritic core. When both a B cell epitope and a T cell epitope are present it is preferable that they are linked in tandem on the same functional group of the dendritic core. Alternatively the T cell epitope and the B cell epitope may be on separate branches of the dendritic core. Preferably, the T cell epitope is a helper T cell epitope; however a cytotoxic T cell epitope may also be used.

Useful T cell epitopes may be derived from the HIV-1 envelope protein. However, it is not necessary that the B cell epitope and the T cell epitope both be derived from the HIV-I gp120 envelope protein. T cell epitopes from different HIV-I proteins (e.g., those encoded by the nef, gag, tat, roy, vif, pol, vpr, vpu, or vpx genes), different retrovirus, or unrelated organisms (e.g., malarial antigens or tetanus toxoid) may be used. T cell epitopes can be identified by a T cell proliferation assay.

Multiple antigen peptide systems and methods for their preparation are described more fully in PCT Publication No. WO 90/11778 and European Patent Publication No. 0 339 695, both of which are hereby incorporated by reference.

As stated earlier, the present invention extends to the preparation of the multiple antigen peptide system herein including the internal adjuvant quality imparted by the macromolecular assemblage approach. The system so prepared may be formulated as a vaccine having a variety of advantages among them the ability to be adapted for both parenteral and oral administration. Accordingly, the invention extends to the preparation of vaccines and their administration to prevent the development of viral infections, and to elicit an immune response, and/or to raise antibodies to such pathogens.

As stated earlier, the invention also extends to the elicitation of an immune response in a host by the administration of compositions including the present multiple antigen peptide system, as well as the immunization of a host by the administration of a vaccine prepared in accordance herewith. The present multiple antigen peptide system may further be prepared with a variety of vehicles including encapsulation within liposomes, for greater efficiency of delivery and concomitantly reduced dosage. The preparation of liposomes is well known in the art.

The amplification that is characteristic of the multiple antigen peptide system of the present invention is made possible by two synthetic components (FIG. 1), (i) A scaffolding consisting of an oligomeric branching lysine is used to amplify the peptide antigen 4-fold to give a multimeric structure. This covalent amplification, known as multiple antigen peptide system (MAPS), has been effective in inducing strong immune responses (12,13). (ii) A lipophilic membrane-anchoring moiety at the carboxyl terminus of MAPS enables further noncovalent amplification by a liposome or micellar form. Such a macromolecular assemblage will amplify the MAP antigens many fold.

Several lipophilic moieties have been studied and are presented herein. The first mentioned and the one that has proved particularly successful is the tripalmitoyl-S-glyceryl cysteine (P3C). P3C, which is a lipoamino acid from *Escherichia coli*, is a B cell mitogen, a nontoxic adjuvant, and can induce CTL in vivo when covalently linked to a peptide antigen (14).

In addition and as illustrated in Example 3 later on herein, palmitoyl lysine has also been prepared and tested with efficacy, and the invention accordingly extends to the use of this lipophilic structure as well.

The antigen for the presently illustrated model is located in the third variable domain (V3 loop) of gp120, the envelope glycoprotein of HIV-I, which is the principal target for vaccine development against AIDS (4). The V3 loop of IIIB strain, amino acid sequence 291–343, contains an invariant disulfide bridge and a type-II β turn with the sequence Gly-Pro-Gly at its crest. Antibodies raised to the V3 loop neutralized the in vitro infectivity of HIV, and the principal neutralizing determinant has been found to be centered at the β turn. Our previous studies in mice (15) have found that a 24-residue peptide of the V3 loop, referred to as B1 (sequence 308–331) and SEQ ID NO: 12 in co-pending application Ser. No. 07/744,281, abandoned in favor of continuation application Ser. No. 08/120,310, filed Sep. 13, 1993, now abandoned, contains the minimal sequence that consists of neutralizing and T-helper epitopes. In addition, this B1 sequence also contains a T-cytotoxic epitope (sequence 315–329) (6). As shown herein, a vaccine model using the peptide B1 by the macromolecular assemblage approach (referred to as B1 in a tetravalent MAPS (B1M format linked to P3C (B1M-P3C) induces specific antibodies against gp120 that neutralize virus infectivity in vitro and elicits CTL in vivo.

The following examples illustrate the preparation of vaccines in accordance with the invention, and further, present data confirming their utility.

EXAMPLE 1

In the following experiments the preparation and comparative testing of a model vaccine based on the present invention is set forth. As a review of the following data will reveal, the vaccine exhibited both improved humoral and cytotoxic activity.

Materials and Methods

Synthesis of B1M-P3C. Synthesis was accomplished manually by a step-wise solid-phase procedure (16) on 9-flourenylmethoxycarbonyl (Fmoc)-Ala-OCH$_2$-resin (17) (0.3 mmol/g of resin). After removal of the Fmoc group by 20% piperidine in dimethylformamide, the Ala-resin was coupled to a premade unit of Fmoc-Lys (P3C) (1.1 molar equivalent) via dicyclohexylcarbodiimide/hydroxybenzotriazole in CH$_2$Cl$_2$. The P3C was prepared as described (14, 18) and contained the configuration of N-palmitoyl-S-[2,3-bis-(palmitoyloxy)-(2RS)-(propyl)]-(R)-cysteine. Two consecutive serines as a linker were coupled to the Lys(P3C) before adding the two levels of Fmoc-Lys(Fmoc) to give a tetra-branching [Fmoc-Lys(Fmoc)]$_2$-Lys-Ser-Ser-Lys(P3C)-Ala resin. The protecting group scheme for the synthesis was as follows: Fmoc for the N$^\alpha$ amino group and the tertbutyl side chain protecting groups for the trifunctional amino except Arg(Pmc) and Asn(Trt). Three equivalents of Fmoc-amino acid were used for each coupling by the DCC/HOBt method. Coupling was monitored by the qualitative ninhydrin test (19). Deprotection by 20% piperidine in DMF (10 min) was preceded by a 2-min wash. The completed peptide was cleaved from the resin by CF$_3$CO$_2$H/2% dimethylsulfide/2# anisole/1% ethanedithiol. The MAPS peptides were purified by precipitations in CF$_3$CO$_2$H/tertbutyl methyl ether. Similarly, synthesis of B1 was accomplished by the Fmoc/tertbutyl strategy and the peptide was purified by reverse-phase HPLC. All peptides gave satisfactory amino acid analyses.

Preparation of positively charged liposome

Liposomes were prepared as described by Gregoriadis et al. (20). Briefly, 56 mg of egg lecithin, 8.4 mg of cholesterol and 1.8 mg of stearylamine were solubilized in CHCl$_3$ in a 100 ml round bottom flask. P3C (0.24 mg) was added to liposomes made with B1M. The organic solvent was removed under vacuum using a rotary evaporator to form a thin film of lipid on the wall of the flask. After drying, nitrogen was kept flushing in the flask for 10 min. Two millileters of 10 mM at pH 7.4, containing 2.5 mg of peptide, was added into the flask. Shaken manually for 10 min, the suspension was then allowed to stand at room temperature for 2 hr. The resulting milky solution was sonicated 45 min (Laboratory Supply, Indianapolis) until the solution became opalescent. After sonication, free B1M-P3C was separated from the liposomes on Sepharose 6B; liposomes were then filtered on 0.45 µm filter and kept under nitrogen.

Immunization procedure and ELISA.

Dunkin-Hartley guinea pigs (3 per group) were immunized subcutaneously with 100 µg of peptide on day 0 and 14, and with 50 µg on days 30 and 45. They were bled two weeks after the last boosting. Control guinea pigs were immunized with the same protocol using a noncovalent mixture of B1M, P3C, and liposome. BALB/c mice (5 per group), 6 to 8 weeks old, were immunized intraperitoneally four times with 1 to 100 µg of B1M-P3C at two to three weeks intervals and bled two weeks after the last boosting. Control mice were immunized with a noncovalent mixture of 50 µg of B1M, P3C and liposome. Antisera were used without purification. ELISA was used to test antisera for their ability to react with B1 (5 µg per well) or recombinant gp120, IIIB isolate (0.1 µg per well) (Repligen, Cambridge, Mass.).

Functional assays.

Fusion inhibition assay was performed on CD4 positive cells CEM-T4 (ATCC) which were infected with either wild type WR isolate or recombinant vaccinia virus (vPE16 recombinant vaccinia vector expressing the HIV-1 envelope glycoprotein gp160 of the IIIB isolate provided by Dr. B. Moss, obtained through the AIDS Research and Reference Reagent Program, division of AIDS, NIAID) at multiplicity of infection of 10. Antisera were added to the cultures 1 hr post infection and syncytia were counted 24 hr post infection (15). For CTL assay, BALB/c mice were immunized with 100 µg of antigen. Three to eight weeks later, immunized spleen cells ($2.5 \times 10^6$ per ml) in RPMI 1640 medium/10% fetal calf serum/2 mM glutamine/50 µm2-mercaptoethanol/antibiotics (GIBCO), complete culture medium were restimulated for 6 days in vitro with 0.4 µM of peptide B1 in 24-well culture plates.

The cytolytic activity of the restimulated cells was tested using a 4 hr assay with $^{51}$Cr-labeled syngeneic cells P815 (H-2$^d$). The target cells were infected with vaccinia viruses v-env5 (recombinant vaccinia virus expressing the complete envelope gene of HIV-1 was provided by Dr. S.-L. Hu) at multiplicity of infection of 50, or pulsed with synthetic peptide (0.8 µM for 2 hr at 37° C.) prior to labeling. The % specific $^{51}$Cr release was calculated as 100×[(experimental release—spontaneous release)/(maximum release—spontaneous release)]. Maximum release was determined from supernatants of P815 cells lysed by the addition of 5% Triton X-100 and spontaneous release from target cells incubated alone. SEM of triplicate cultures were all <5% of the mean. Neutralization assay by inhibition of the reverse transcriptase activity was performed as reported by Ho et at. (21) on HIV-infected H9 cells.

IL-2 production and B-cell proliferation.

Splenocytes of mice primed intraperitoneally 10 days before with 50 µg of B1M-P3C were dispensed in 24 well-plates at the concentration of $4 \times 10^6$ cells per well in complete culture medium. Peptides at various concentrations were added to the cell suspension. Medium alone was added to other wells to assess the IL-2 production in absence of antigenic restimulation. After 36 hr incubation at 37° C., supernatants were collected, centrifuged, and added to IL-2 dependent cytotoxic T-lymphoid line (CTLL-2) to determine their IL-2 activity.

Briefly, 50 µl of supernatant was added to 50 µl of CTLL-2 suspension ($8 \times 10^4$ cells per ml) in a 96-well microtiter plate. Cells were harvested after one day incubation. During the last 5 hr of incubation, each well was pulsed with 1 µCi of [$^3$H]thymidine (1 Cl=37 (3 Bq). Results were expressed in units of IL-2 per ml (means of triplicates) for each group. B-cell proliferation assay was performed on spleen lymphocytes grown for 72 hr in RPMI 1640 medium/3.3% fetal calf serum glutamine/2-mercaptoethanol/antibiotics at a cell density of $3.3 \times 10^6$ cells per ml in flat-bottom microtiter plates (0.2 ml per well). Antigens were added at the beginning of the culture. Before harvesting, cultures were pulsed for 24 hr by adding 1 μCi of [$^3$H] thyroidinc to each well. The results are as reported as means of triplicate determinations (standard errors were <10% of the mean) of a representative experiment.

RESULTS

Synthesis of B1M-P3C.

B1M-P3C (FIG. 1) was synthesized in two parts. (i) P3C was achieved in a solution synthesis in six steps according to Wiesmmüller et al. (18) and linked to the side chain ε-amino group of Fmoc-Lys-phenacyl ester. The phenacyl ester protecting group was subsequently removed to give an isopeptide, Fmoc-Lys (P3C). (ii) The synthesis of B1M which contained the B1 antigen and the lysine core matrix was achieved by the solid-phase method (13,16) with Fmoc-Ala-OCH$_2$-resin (17). Fmoc-Lys(P3C) as a premade unit was first attached to the Ala-OCH$_2$-resin, followed by a diserine spacer prior to the synthesis of a trilysine core matrix of MAPS and the B1 sequence. The design of linking P3C to the side chain of the lysine spacer (Ser-Ser-Lys) at the carboxyl terminus of the MAPS was intended to provide flexibility for the P3C to serve as a lipid-anchoring moiety without interfering with the antigen organization at the amino terminus. Because the secondary ester bond in P3C was labile to HF, the solid-phase synthesis was performed with the Fmoc chemistry (22) in combination with the Wang resin (17) so that the final cleavage could be carried out in a mild acid such as $CF_3CO_2H$. The synthesis, performed manually, was rigorously monitored for the completion of each coupling step (22) to avoid deletion peptides. B1M-P3C was obtained after TFA cleavage from the resin support and was purified by repeated precipitations.

The advantage of this direct approach was its simplicity. Other unambiguous routes for the preparation of B1M-P3C by the segment approach have also been developed (23). P3C in B1M-P3C allowed self aggregation in aqueous solution and efficient incorporation in liposomes. About 80% of B1M-P3C was found to be associated with liposomes while only 2% of B1M without P3C was found to be entrapped by liposomes. Both preparations of B1M-P3C in aggregated form in solution (B1M-P3C/free) or associated with positively-charged liposomes (B1M-P3C/liposome) were tested in animals for humoral and CTL responses.

B-cell mitogenic activity and humoral response of B1M-P3C.

Figure 2:
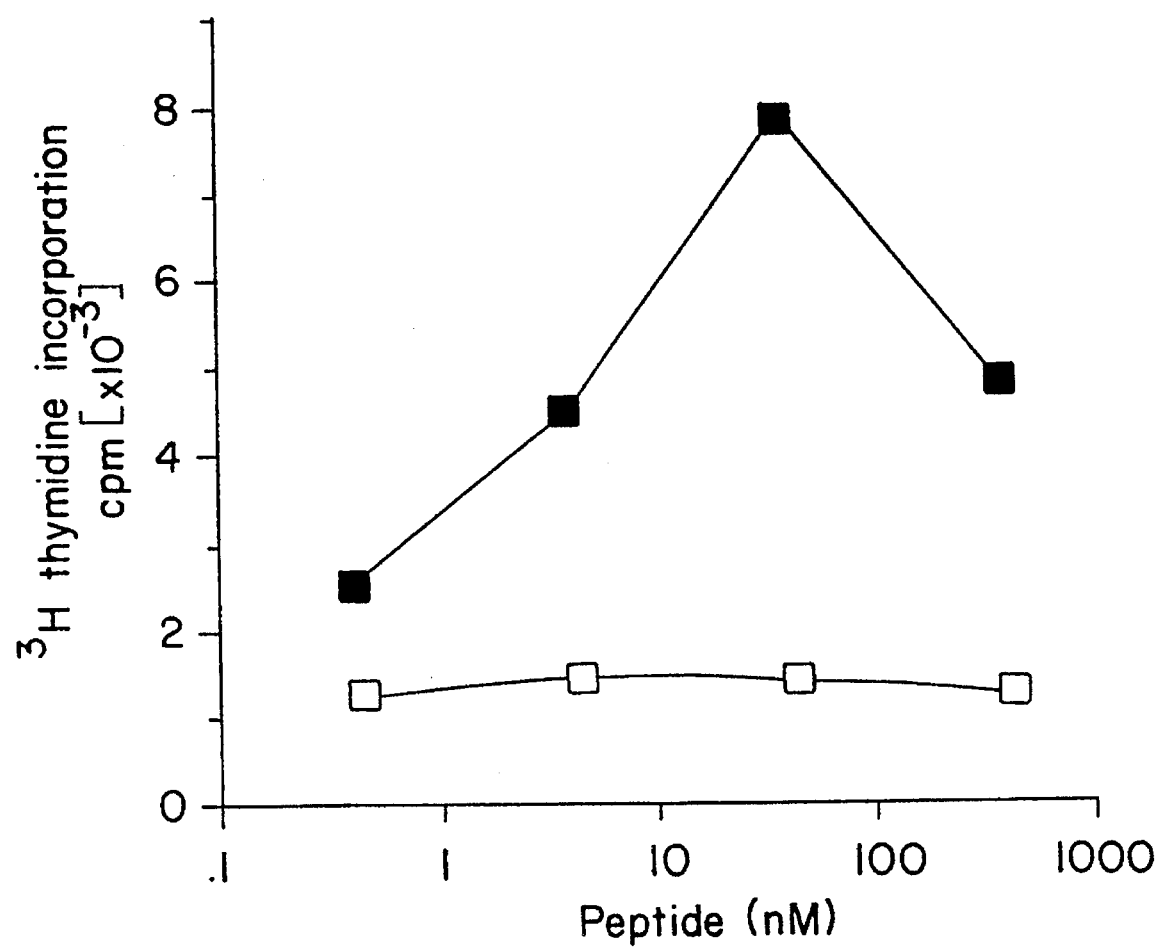
FIG. 2 is a graph of the mitogenic activity of the B1M-P3C. BALB/c mouse spleen cells ($3.3 \times 10^6$ cells/ml) were grown for 72 hr in the presence of B1M-P3C (■) or B1M (□). 24 hr before harvesting, cells were pulsed with 1 µCi [$^3$H]thymidine.

Mouse spleen cells were used to demonstrate that the mitogenic activity of the P3C was retained in B1M-P3C (FIG. 2). The mitogenicity was dose-dependent with increased incorporation of [$^3$H]-thymidine in spleen cells with escalated concentrations of B1M-P3C. B1M without P3C did not show any mitogenic activity.

The ability of B1M-P3C/liposome or free, without any adjuvant, to induce humoral response was studied in mice and guinea pigs. High-titered antibodies were found in sera from animals immunized four times with both preparations and treated with B1 (linear peptide 308–331), B1M, or gp120 in a ELISA assay, the data from which is set forth in Table 1, below.

TABLE 1

Immune Response to B1M – P3C

| Immunogen | Antibody Titer (× 10$^{-3}$)$^A$ | | Inhibition | |
|---|---|---|---|---|
| | Peptide | gp120 | Syncytium formation$^b$ | RT activity$^c$ |
| Mouse | | | | |
| Control | <0.01 | <0.01 | 0 | ND |
| Liposome | 10 | 4 | 20 | 8 |
| Free | 4.3 | 2 | 10 | 8 |
| Guinea Pig | | | | |
| Control | 6.8 | 1.2 | 0 | 0 |
| Liposome | 6.5 | 3.2 | 20 | 8 |
| Free | 8.2 | 3.3 | 10 | 8 |

RT, reverse transcriptase; ND, not done.
$^a$ELISA titers represent the reciprocal of the end-point dilution (serum dilution at which OD is 0.2 unit). Mice were immunized with 100 μg of B1M – P3C, and control group were immunized with 50 μg of a noncovalent mixture of B1M/P3C/liposome.
$^b$Fusion inhibition titers are dilutions reducing the number of syncytial foci by 90%.
$^c$Neutralization titers are the reciprocal of a dilution reducing RT activity by 87%.

There was no significant difference between B1M-P3C/free or B1M-P3C/liposome, but there was a dose-response of titers with increasing immunizing doses. Tilers from mice immunized with 100 μg of B1M-P3C/liposome were 2- and 4 fold higher than those immunized with 50 or 10 μg (data not shown). Both preparations of B1M-P3C elicited antibodies in mice and guinea pigs that showed ability to neutralize HIV as shown by the inhibition of syncytia formation in vPE16-infected cells and the reverse transcriptase activity of HIV IIIB-infected H9 cells (Table 1 ). Control mice immunized with a noncovalent mixture of B1M/P3C/liposome did not develop detectable antibodies against B1 or gp120. In contrast, this noncovalent mixture elicited significant titers in guinea pigs. However, both sera of control mice and guinea pigs had no effect on the ability to inhibit the syncytia formation or the reverse transcriptase activity.

Cytokine production and CTL response.

Figure 3:
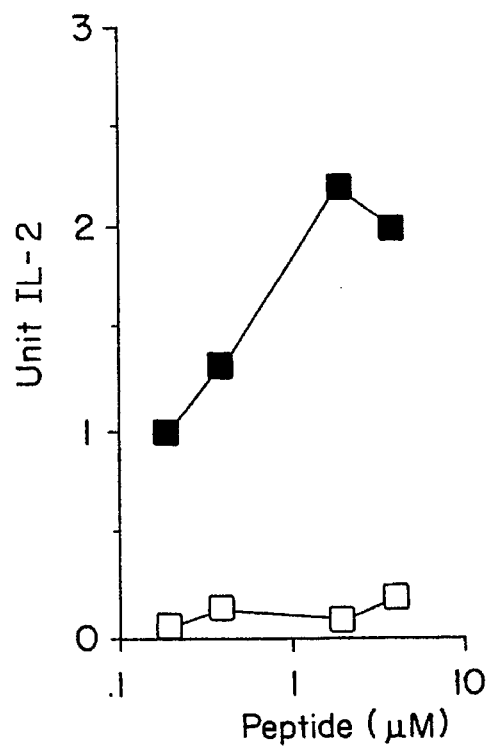
FIG. 3 is a graph showing IL-2 production of lymphocytes primed with B1M-P3C. Splenocytes from mice immunized with 50 µg of B1M-P3C were cultured in presence of B1 (■) or a control peptide from the malaria circumsporozoite protein [(Asn-Ala-Asn-Pro)$_3$MAP] (□).
Figure 4A:
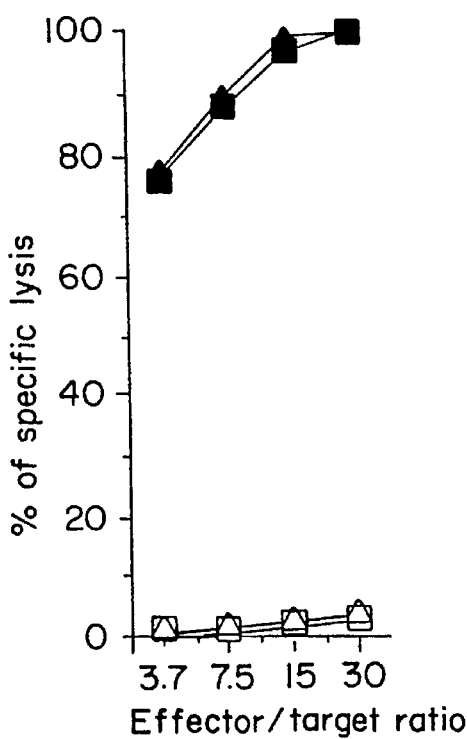
FIG. 4 is a graph showing induction of HIV-1 envelope-specific CTL. Spleen cells from mice immunized with B1M-P3C in liposome (A) or free (B) were restimulated with B1. Cytotoxic activity was tested on P815 target cells alone (○), presensitized with a control peptide T1 derived from the C4 of gp120, aa 429–443 (△), presensitized with B1(■), infected with vaccinia virus WR (□) or with vaccinia virus v-env5 expressing gp160 (▲).

B1M-P3C induced CD4$^+$ T-helper cell response in immunized mice (FIG. 3). IL-2 activity was found in the supernatant of spleen cells restimulated with B1. A control and unrelated peptide from the CS protein [(Asn-Ala-Asn-Pro)$_3$MAP)] did not show any activity. Spleen cells of mice immunized with B1M-P3C free or in liposome were assayed for their ability to lyse target cells preincubated with B1 or infected with vaccinia virus expressing gp160. As shown in FIG. 4, B1M-P3C, in liposome or free, elicited CD8+CTL in mice against vaccinia virus infected cells (v-env5) and B1 peptide-coated cells. The CTL response was mediated by CD8+lymphocytes (unpublished work).

EXAMPLE 2

In the following experiments, further vaccines were prepared and tested both as to their preparation and as to their administration. The results are further confirmatory of the effectiveness and particularly of the adjuvant capability that the present system manifests.

As discussed herein, the vaccine model (B1M-P3C) is designed to mimic the glycoprotein gp120 anchored on the virus external membrane. It contains four components (starting from the amino terminal of the construct): four identical peptide antigens (aa 308–331), an oligolysine scaffolding (Lsy$_2$Lys), a spacer (Ser-Ser-Lys) and a hydrophobic moiety (P3C) attached to the Lys side chain of the tripeptide spacer. Because of the hydrophobicity of P3C, B1M-P3C is able to aggregate in aqueous solution or anchored in liposomes to form a large macromolecular assemblage. Both preparations were tested in mice to show their efficacy in the induction of antibodies and CTL response.

Materials and Methods

B1M peptide was synthesized by stepwise solid phase synthesis on Fmoc-Ala-Wang resin. It was covalently linked to the premade P3C using 2 serine residues as a spacer (30). Liposomes were made following the method of Gregoriadis (20). BALB/c mice (5 each group) were immunized i.p. or s.c. with 50 μg of B1M-P3C free or in liposomes (using phosphate-buffered saline as vehicle) and boosted three times at 2 week intervals. Sera were collected 15 days after the last boost and tested in enzyme-linked immunosorbant assay (ELISA) using alkaline phosphatase conjugate-antibodies (Southern Biotechnology) and p-nitrophenyl phosphate substrate (Sigma) as the detection system. Cytotoxicity assays were performed with the splenocytes of the immunized mice: $8\times10^6$ cells/well were cultured in vitro with B1 peptide (0.4 μM) for 6 days. Effecter cells were tested in a standard 4 h assay using Na$_2^{51}$CrO$_4$ (New England Nuclear)-labeled target cells ($5\times10^4$ cells/well).

RESULTS

The mouse antibody response after i.p. and s.c. immunizations was evaluated in ELISA as shown in Table 2, below.

TABLE 2

| Induction of Antibody and Cytotoxic Responses | | |
|---|---|---|
| | Antibody Response[a] (titer) | Cytotoxic Response[b] (% lysis) |
| | Intraperitoneal Immunization | |
| B1M + P3C + liposome[c] | >100 | ND[d] |
| B1M – P3C | 2000 | 60 |
| B1M – P3C/liposome | 7000 | 80 |
| | Subcutaneous Immunization | |
| B1M – P3C | 700 | 40 |
| B1M – P3C/liposome | 460 | 98 |

[a]Mouse immune sera were tested in ELISA using peptide-coated microriter plates and alkaline phosphatase-conjugate antibody direct against mouse IgG. The results are expressed as geometric means of the titers (reciprocal of the serum dilution at which the absorbance produced by the immune serum is 0.2 units).
[b]Effecter T-cells were added to syngeneic target cells P815 coated by the B1 peptide at E:T ratio of 15:1. The values represent the average of triplicate determinations of a representative experiment.
[c]Control group immunized with B1M not covalently linked to the P3C lipopeptide and not entrapped in liposomes.
[d]ND - not done The results showed that the induction of anti-V3 antibodies depended on the route used for the immunization. The i.p inoculation gave 3 to 15 fold higher response than s.c. inoculation. Furthermore, the antisera induced by i.p. immunization were neutralizing. Analysis of the antibody isotypes in the B1M-P3C/liposome immune sera (FIG. 5) showed that IgG1 was by far the dominant subclass. This result is in agreement with other studies showing that envelope peptides are almost exclusively IgG1 restricted.

Figure 6:
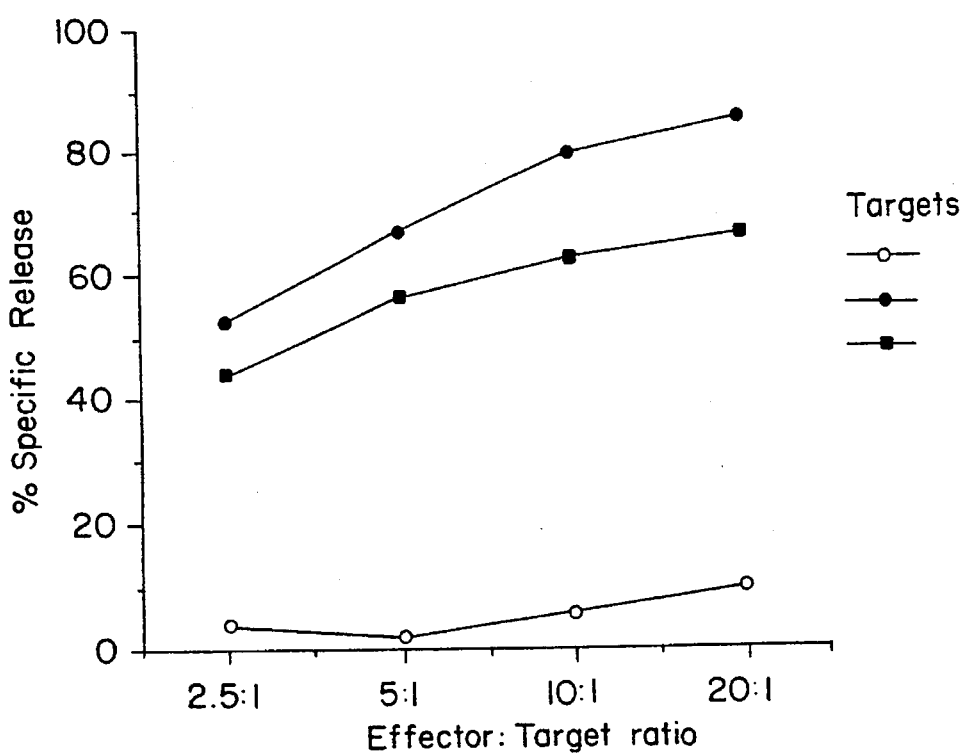
FIG. 6 is a graph showing the cytotoxic response of T-cells derived from mice immunized with B1M-P3C/liposome. The cells were taken 5 months after the last boost and restimulated in vitro with the V3 peptide. CTL activity was assayed on untreated, or recombinant vaccinia virus (v-env5, containing the HIV-1 envelope gene of the BRU isolate) infected target cells (P815), or cells preincubated with B1 peptide (0.8 µM).

The cellular immune response induced by the two preparations was then analyzed. The murine splenocytes were restimulated in vitro and tested for their ability to lyse syngeneic target cells preincubated with the V3 peptide (Table 2). In contrast to a significant difference in the humoral response induced by the i.p. or s.c. immunization, substantial CTL response was produced by either route of immunization. In addition, a long-term T-cell memory was induced, since there was no decrease in the cytolytic activity of the immunized mice 5 months after the last boost with B1M-P3C/liposome. As shown in FIG. 6, the lysis of peptide-coated targets paralleled that of gp160-vaccinia infected cells, whereas no killing of untreated targets was observed.

An important requirement for an ideal candidate vaccine is the capacity to induce T-cell responsiveness along with the stimulation of antibody production (31). The above data shows the feasibility to elicit both humoral and CTL responses with a peptide-based MAP model (B1M-P3C), without the use of an extraneous adjuvant. The route of i.p. injection elicits in mice an antibody response stronger than the s.c. inoculation. B1M-P3C in liposomes also provide an useful formulation for presenting the antigen to the immune system. The rationale for anchoring B1M-P3C on liposomes was to mimic the external appearance of the virion, particularly of the surface protein. Furthermore, the lipid anchor, P3C, serves a dual role, as a built-in adjuvant and a lipid-anchoring moiety. We also show that B1M-P3C induces a long-lasting T-cell immunity. This result is encouraging since it overcomes problems associated with adjuvants such as alum, that do not generate a good cellular response, and with vaccination protocols that do not lead to a lasting T-cell memory.

DISCUSSION

Described herein is the rational design of a totally synthetic peptide-based vaccine that induces neutralizing antibody and CTL as well as a vaccine that is safer and more versatile than a whole virus or viral protein vaccine. As set forth above, a macromolecular assemblage approach is used to produce a multimeric form of peptide antigen, B1M-P3C, that consists of a lipophilic membrane-anchoring moiety covalently linked to a MAPS core matrix and four dendritic arms of peptide antigens derived from the V3 loop of the gp120 envelope protein of HIV-1. Mice antisera against B1M-P3C neutralize the virus infectivity as shown by the inhibition of syncytium formation and reverse transcriptase, induce T-helper response as shown by the IL-2 production, and elicit CD8+CTL that lyse syngeneic cells expressing gp160 on their cell surface. Furthermore, the B1M-P3C produced long term T-cell memory as the CTL of the immunized mice remained undiminished 5 months after the last boost immunization (24).

These results are particularly pertinent to the development of a synthetic vaccine against AIDS since the predominant vaccine strategy has focused on neutralizing antibodies rather than cell-mediated immunity, which may be an equally effective mechanism to overcome cell-to-cell virus transmission in HIV infection. Subunit protein administered with a clinically acceptable adjuvant such as gel of aluminium or calcium salt is usually insufficient to elicit CTL response, particularly CD8 +restricted as shown by the results of Orentas et al. (25) who found CD4+specific CTL by a gp160 subunit vaccine. Subunit vaccine expressed by live vectors such as vaccinia virus (26) may overcome this limitation but will need further development to define various adverse reactions in humans. The ideal vaccine may be eventually derived from the inactivated whole or attenuated virus, but the risk and long latency associated with the infection have so far limited the enthusiasm for its development.

EXAMPLE 3

In this example, the preparation and testing of an alternative lipophilic moiety is presented. Specifically, the lipophilic moiety was prepared from palmitoyl lysine (PL), and as reflected by the ensuing results, a structure comprising PL of alternating chirality was particularly effective. The details of the preparation and testing of the lipoMAPs based on this lipophilic moiety follow below.

Materials and Methods

Synthesis of MAP-palmitoyl lysine conjugates with symmetrical core matrix (B2SM-Pln, n=1–4).

The B2SM-Pln were manually synthesized by solid phase peptide synthesis on Boc Aln OCH$_2$-Pam resin (17) (0.10 mmol/g) using a combination of Boc and Fmoc strategy. Removal of the Fmoc group was carried out by 20% piperidine in dimethylformamide. Removal of Boc group was carried out by 50% TFA in dichloromethane followed by washing with dichloromethane and neutralization with diisopropylethylamine/dichloromethane/dimethylformamide (1:9:11). Couplings of amino acids (4 molar equivalents) were carried out with the coupling reagent HBTU/diisopropylethylamine in dimethylformamide. The stepwise syntheses were described below.

Palmitoyl lysine. After removal of the Boc group on the resin (Boc-Ala-OCH$_2$-Pam-resin), one or more rounds of Fmoc-Lys(Boc) was coupled sequentially to the alanyl resin. The N$^\epsilon$-Boc groups on Lys were then removed and the palmitic acids (6 molar equivalents) were coupled by symmetrical arthydride method using dicyclohexylcarbodiimide (3 molar equivalents) to form Fmoc-[Lys(Pal)]$_n$-Ala-OCH$_2$-Pam-resin.

Ser-Ser linker. The N$^\alpha$-Fmoc on the Lys(Pal) was then removed. Two consecutive rounds of Boc-Ser (Bzl) were coupled by the HBTU method.

Symmetrical MAP core. After the removal of Boc group on Ser(Bzl), Fmoc-Lys(Boc) was coupled. N$^\alpha$-Fmoc group on Lys was removed and Boc-β-Ala (0.4 mmol/g) was coupled to furnish the first level branching. After removal of Boc in Boc-β-Ala-Lys(Boc), the above steps were repeated for a second level branching to give a tetravalent MAP and two levels of symmetrical branching. Note, 0.8 mmol/g of Boc-β-Ala was used in the second round of branching.

Peptide antigen. The peptide antigen B2 having an amino acid sequence 312–329 of the third variable domain of gp120, the envelope glycoprotein, of HIV-1 strain IIIB, was coupled stepwise using the Boc/HBTU chemistry. The protecting groups for the trifunctional amino acids: Thr(Bzl), Ser(Bzl), Lys(ClZ), ArgCTos). For each coupling step, 1.6 mmol/g of Boc amino acids were used since the resin had been amplified from 0.1 mmol/g to 0.4 mmol/g.

Cleavage and workup. The resin (0.5 g) was stirred in HF solution (0.3 ml of thiocresol, 0.7 ml of p-cresol and 9.0 ml of HF) at 0° C. for 1 h followed by extraction with 8M urea in 0.1M Tris-HCl buffer, pH 7.4. The organic scavengers were removed by dialysis against 0.1M Tris-HCl buffer, pH 7.4 with decreasing urea concentration to 0M in 24 hours. All synthetic MAP-PLs gave satisfactory results of amino acid analyses and mass spectroscopy (FAB or laser desorption).

Synthesis of MAP-P3C with a disulfide linkage (P3C-Cys-OMe)$_2$. To an ice-cold solution of tripalmitoyl-S-glyceryl cysteine (P3C) (0.91 g, 1 mmol), dimethylcysteine HCl (0.20 g, 0.6 mmol) and triethylamine (1.2 mmol) in THF (5 ml), HOBt (0.14 g, 1 mmol) and DCC (0.23 g, 1.05 mmol) were added. The solution was stirred at 0° C. for 1 hr and at room temperature for 1 hr. Ethyl acetate (10 ml), chloroform (50 ml) and saturated NaHCO$_3$ were added, and the resulting solution was then washed with 5% citric acid, NaHCO$_3$ and water (3 ml each). After being dried over Na$_2$SO$_4$ and concentrated, pure product (0.63 g) was obtained by recrystallization from hexane, m.p., 77.0–78.0 C, R$_f$=0.90 (ethylacetate:hexane/3:7).

P3C-Cys-OMe. To a degassed suspension of (P3C-Cys-OMe)$_2$ (2.46 g, 1.20 mmol) in chloroform, triethylamine (0.39 mL0 and DTr (0.82 g, 5.20 mmol.) were added under nitrogen. The clear solution was stirred for 2 hr, washed with 5% citric acid (3×25 ml) and water (2×25 ml), and dried over Na$_2$SO$_4$. The colorless solid was obtained (1.96 g 80% yield) by recrystallization from methanol and drying over P$_2$O$_5$ under vacuum, m.p. 75°–77° C. R$_f$=0.76 (ethylacetate:hexane/3:7).

Figure 10A:
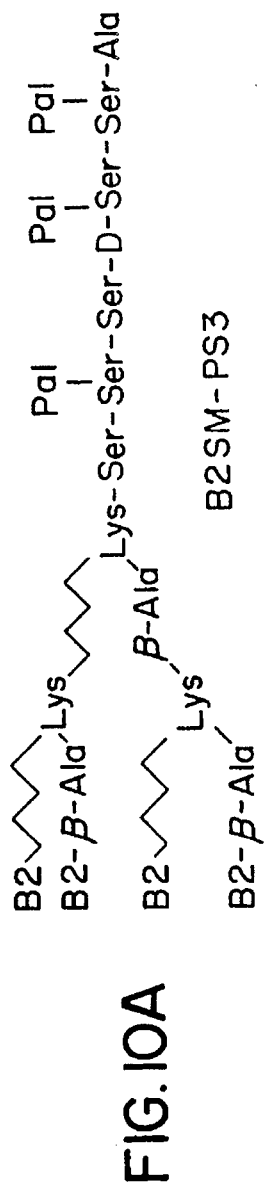
FIG. 10 comprises a schematic representation of MAP conjugates containing (A) palmitoyl groups linked to the side chain of serines (B2SM-PS3); (B) L-Ser-D-Ser linker (B2SM-D-PL3); (C) zero to four palmitoyl lysines.
Figure 10B:
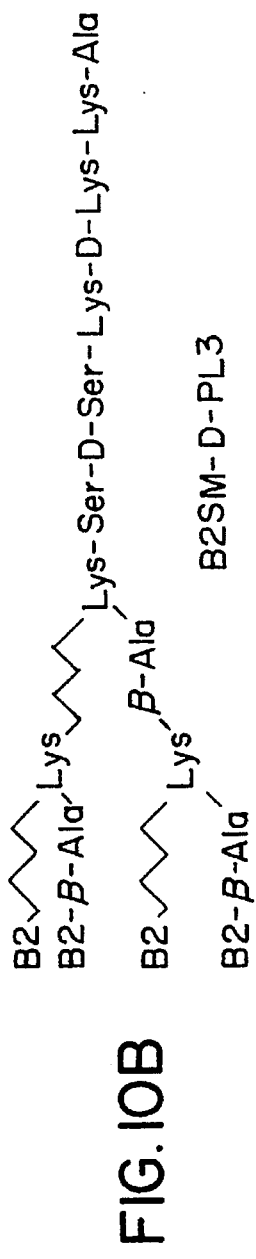
Figure 10C:
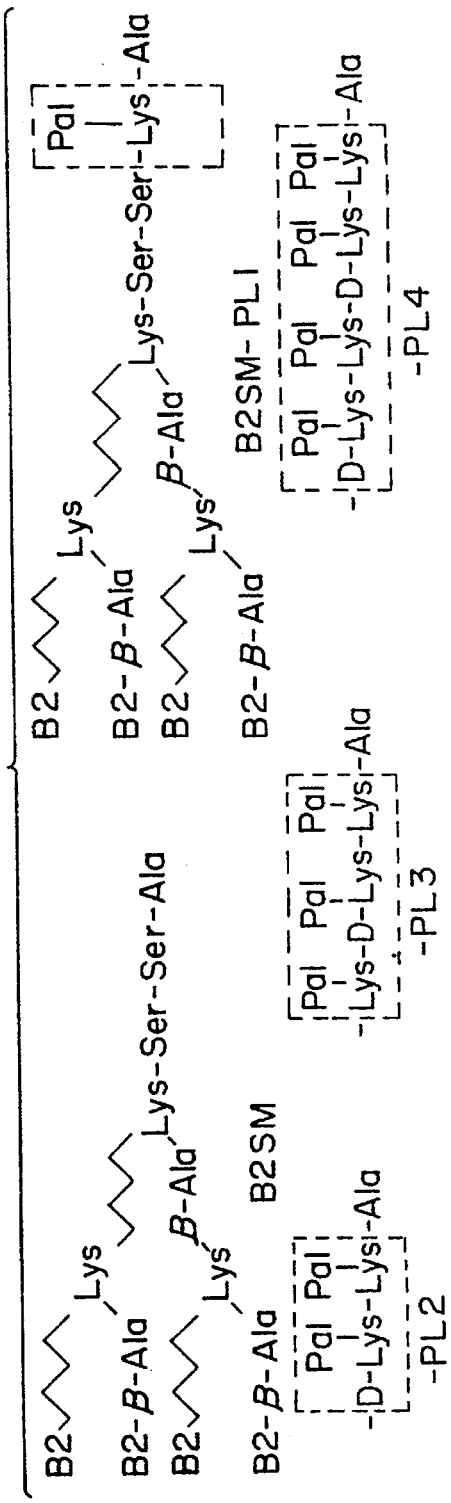
Figure 11:
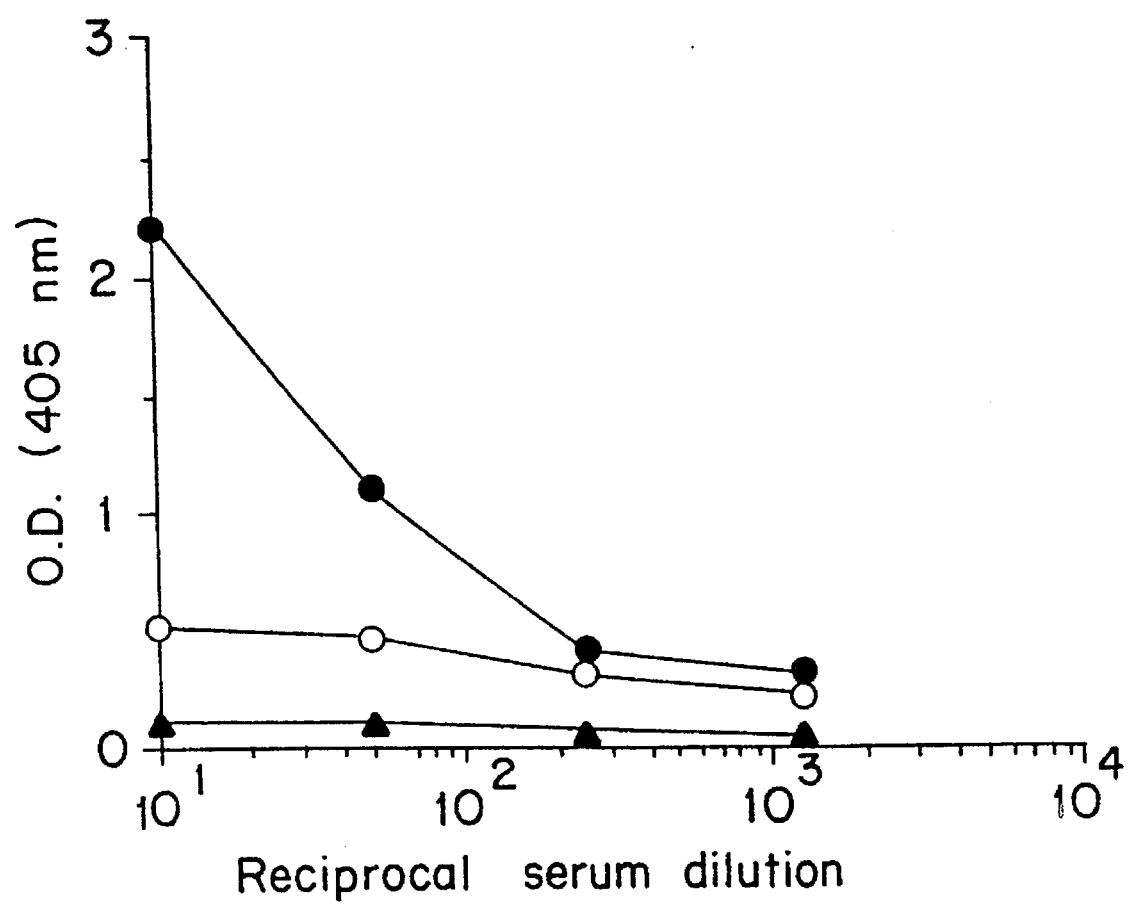
FIG. 11 comprises graphs showing the immunogenicity of MAP-PLs, varying the linker and of the lipophilic moiety. Antibody response induced in CD-1 mice by the immunization with B2SM-PL3 (●), B2SM-D-PL3, (o), B2SM-PS3 (▲), as measured by ELISA.
Figure 12A:
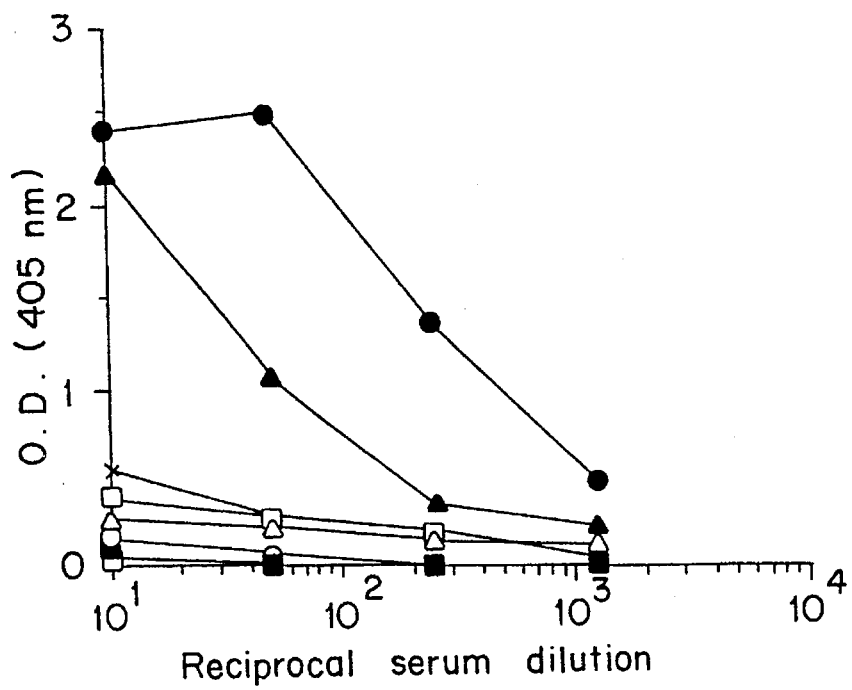
FIG. 12 shows the influence of increasing numbers of palmitoyl side chain on the immunogenicity of B2SM-PLs. The antibody response was measured by ELISA in the sera of mice immunized with B2SM-PL2/liposomes (●), -PS3/liposome (▲), -PLA/liposomes (■) or with the free constructs B2SM (x). B2SM-PL1 (□), -PL2 (o), -PL3 (Δ), -PL4 (◇). (A) antibody response against B2 peptide; (B) against gp120.
Figure 12B:
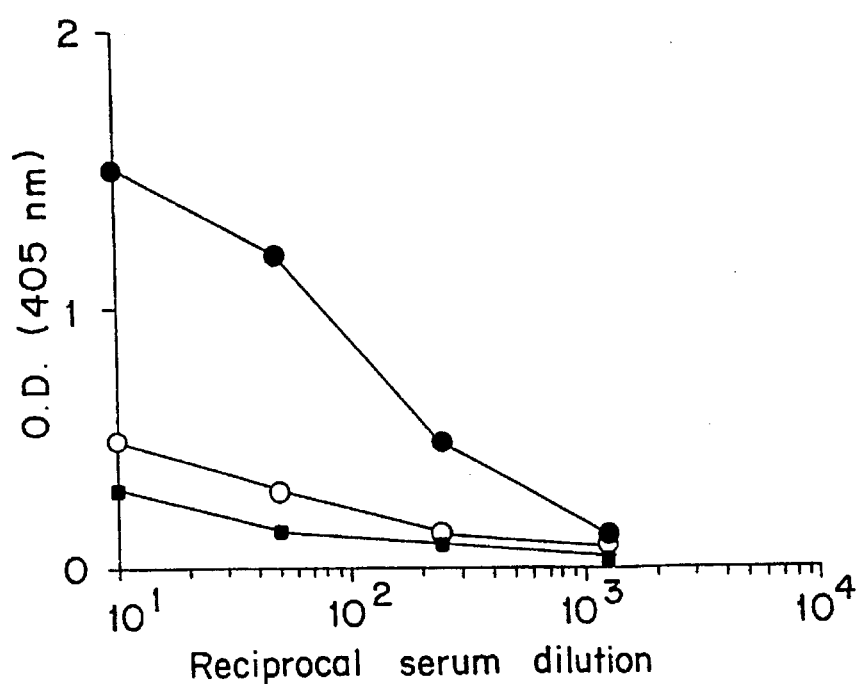
Figure 13A:
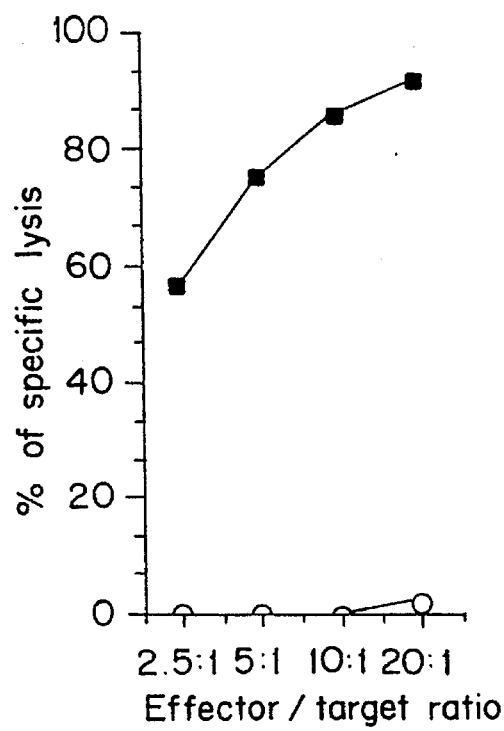
FIG. 13 comprises graphs illustrating the induction of anti-HIV CTL. Cytotoxic activity in the spleen cells of BALB/c mice immunized with B2SM-PL2 free (A) or B2SM-PL2/liposome (B) was assayed on syngeneic P815 target cells coated with the antigenic peptide (closed symbols) or an untreated P815 cells (open symbols).
Figure 13B:
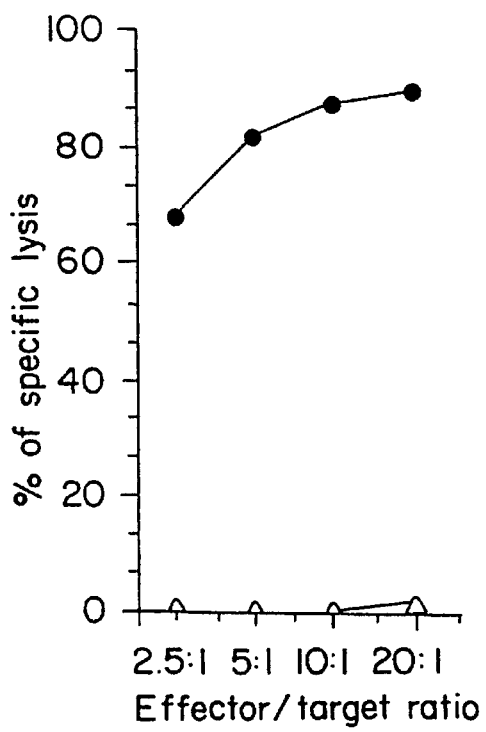
Figure 14:
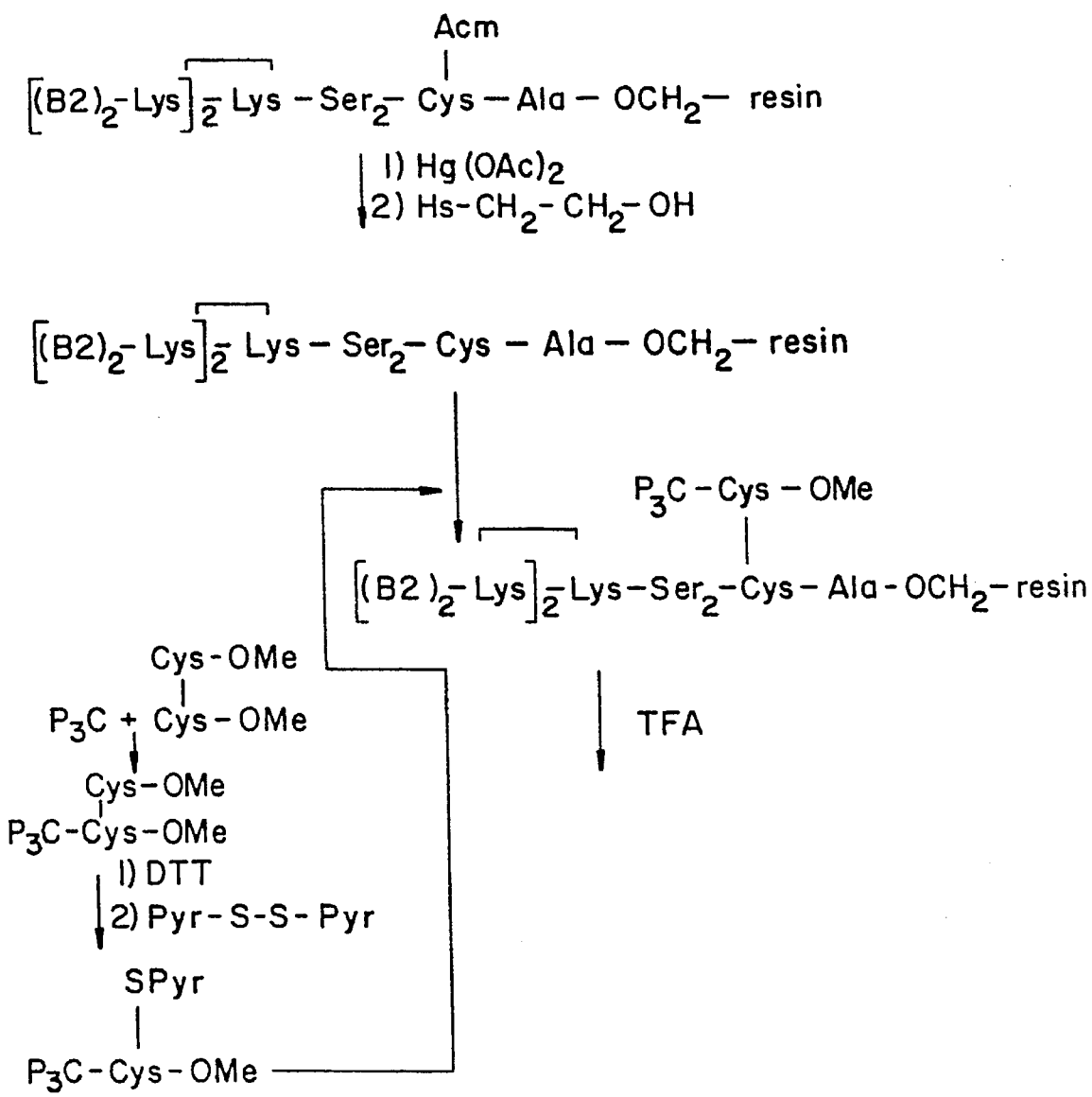
FIG. 14 comprises a structural depiction of the preparation of tripalmitoyl cysteine conjugate of MAP bearing B2 peptides (B2M-P3C) with a disulfide linkage.

P3C-Cys(Pys)-OMe. The solution of P3C-Cys-OMe in chloroform (10 ml) was added dropwise into the solution of 2,2'-dithiopyridine (0.95 g) and glacial acetic acid (0.15 ml) in absolute ethanol (4 ml). The mixture was stirred for 20 hr. During this period, the solution color turned yellow due to release of 2-pyridinethionol. The solution as concentrated to about 3 ml and passed through a silica gel column (ethylacetate:hexane/1:2 to 2:0). The first colorless fraction was the product (1.47 g, 72.3%), m.p. 68.0°–69.0° C., R$_f$=0.78 (ethylacetate:hexane/2:1). $^1$HNMR, 350 mHz (FIG. 10). $^{13}$CNMR 350 mHz (FIG. 11). Cald: C 66.55, N 3.70, H 10.04, S 8.46. Found: C 66.79, N 3.65, H 9.90, S 8.,45, MS: m/z+1137.

B2M-Cys(P3C-Cys-OMe)-Ala. B2M-Cys(Acm)-Ala-Pam-resin was synthesized in Fmoc/TFA chemistry as described above. The protecting group acetamidomethyl (Acm) on the cysteine was removed with Hg(OAc)$_2$ on the resin as described (12). The B2M-Cys-Ala-Pam resin (10 μmol) in chloroform/propanol (4:1, 8 ml) reacted with P3C-Cys(PyS)-OMe (45 mg, 40 μmol) in the presence of triethylamine for 24 hr. The yellow by-product 2-pyridinethiol released quantitatively (UV 343 nm, ε=8080), which was used to monitor the reaction. The unreacted P3C-Cys(PyS)-OMe was recovered in the washings with methanol. The yield was 33 to 54%. Satisfactory results of amino acid analyses were obtained after oxidization of cysteine with performic acid. The product was purified through gel filtration (Sephadex G75) or directly used for preparation of liposomes, since unreacted MAP peptide did not incorporate into liposomes and was separated by gel filtration later.

Preparation of liposomes

MAP-PLs were incorporated into liposome with detergent-dialysis method (13). In a round-bottle flask, phosphatidyl choline (5 mg), cholesterol (5 mg) and octylglucoside (100 mg) were dissolved in about 1 ml of acetone and evaporated under nitrogen. The residue was re-dissolved in diethyl ether and re-evaporated to form a lipid film on the glass wall. A detergent solution (23 mg of octylglucoside in 5 ml of 0.30M NaCl aqueous solution) containing 0.5 mg of MAP-PLs was added to the dry lipid film and dispersed with vortexing. The resulting clear liquid was dialyzed for 36 hr against three 2-liter changes of PBS (pH 7.4). Purification of liposome monitored at 225 nm was carried out by gel filtration on sterile Sephadex G-150 with PBS.

Immunization procedure

Outbred female CD-1 mice or inbred female BALB/c mice (Jackson Laboratories, Bar Harbor, Me.) were injected intraperitoneally with 50 µg of the antigen, free or in liposomes, using phosphate-buffered saline as vehicle, for three times at two week intervals. Sera were collected fifteen days after the last boost. The antibody response was analyzed by enzyme-linked immunosorbent assay (ELISA) using plates coated with B2 peptide (5 µ/g well) or gp120 (1 µg/well), kindly provided by Dr. A. Profy (Repligen). Serial dilutions of the sera were added to the wells and the bound antibodies were detected using goat alkaline phosphatase-conjugate antibody (Sigma) and p-nitrophenyl phosphate substrate (Sigma).

Cytotoxicity Assay

Spleen cells from the immunized BALB/c mice were cultured in vitro for 5 days in RPMI 1640 medium supplemented with 10% fetal bovine serum, 2 mM glutamine, $5\times10^{-5}$M 2-mercaptoethanol and antibiotics) in presence of B2 peptide (0.4 µM).

The cytotoxic activity was tested in a 4 hr assay against $^{51}$Cr-labeled syngeneic P815 cells untreated or preincubated with B2 peptide (0.8 µM). The percentage of specific $^{51}$Cr release was calculated as 100 (experimental release—spontaneous release)/(maximum release—spontaneous release). Maximum release was determined from supernatants of P815 cells lysed by the addition of 5% Triton X-100 and spontaneous release from target cells incubated alone.

RESULTS

Synthesis of MAP-PLs conjugates

The basic design of the model used for our study in shown in FIG. 1. It consisted of four components: an antigen, a core matrix, a hydrophilic linker and a lipophilic carboxyl end. The selected peptide antigen for this study was an 18-residue peptide, (amino acid sequence 312–329; referred to as B2), which is derived from the third variable domain (V3 loop) of gp120, the envelope glycoprotein of HIV-1 strain IIIB (4). This 18-residue sequence includes T-helper and T-cytotoxic epitopes (6) and has been shown to elicit excellent antibody titers in mice using the MAP system in Freund's adjuvant (16), or as a covalent conjugate with the P3C in liposomes (32). The branching core matrix was made by three units of β-alanyl-lysine. Since β-alanyl-lysine contains amino groups nearly equal in distance from the α-carbon of the lysine, the resulting core matrix is nearly symmetrical. It may also have the advantage of greater flexibility than the conventional asymmetric core matrix consisting only of lysine. The carboxyl end of the core matrix contains a hydrophilic dipeptide linker, Ser-Ser, followed by a series of palmitoyl lysines which are used as anchors to the lipid matrix. From molecular modeling study (Quanta, Silicon Graphic), these palmitoyl lysines are best positioned in alternating chirality (D or L) so that the lipid anchors are in parallel orientation required for inserting into liposome membrane.

The synthesis of these models was carried out stepwise by the solid-phase method and was not much different from the methodology that our laboratory first reported for the preparation of MAP systems. Since the conjugations of all parts in these MAP-PLs are amide bonds, they can be synthesized stepwise as a complete unit by the Merrifield solid phase method using a combination of Boc and Fmoc chemistry. The lipophilic carboxyl peptides could be built by two methods. In the first method, palmitoyl lysine was incorporated as Boc-Lys(Fmoc) and then the Fmoc group was removed so that palmitic acid was conjugated to the side chain. Alternatively, the palmitoyl lysine could be premade in solution chemistry and incorporated as a single unit.

Next, to form the core matrix, β-Ala-Lys was incorporated sequentially as Fmoc-Lys(Boc). Deprotection of the Fmoc and incorporation of the Boc-β-Ala produced the desired β-Ala-Lys unit on the resins. Again, a premade dipeptide of Boc-β-Ala-Lys(Boc) could be incorporated as a single unit to reduce several repetitive steps in solid phase manipulations. Once the core matrix was completed, the antigens to be amplified fourfold were synthesized sequentially to produce the desired model. The MAP-PLs containing antigens and palmitoyl lysine were cleaved from the resin, extensively dialyzed against decreasing concentrations of urea-buffer solution and then purified by gel permeation chromatography. The products showed the expected amino acid ratio by amino acid analysis. Seven MAP-PLs were prepared to investigate the various structural contributions to immunogenicity (FIG. 4).

Immunogenicity of MAP-PLs in liposomes

Figure 5:
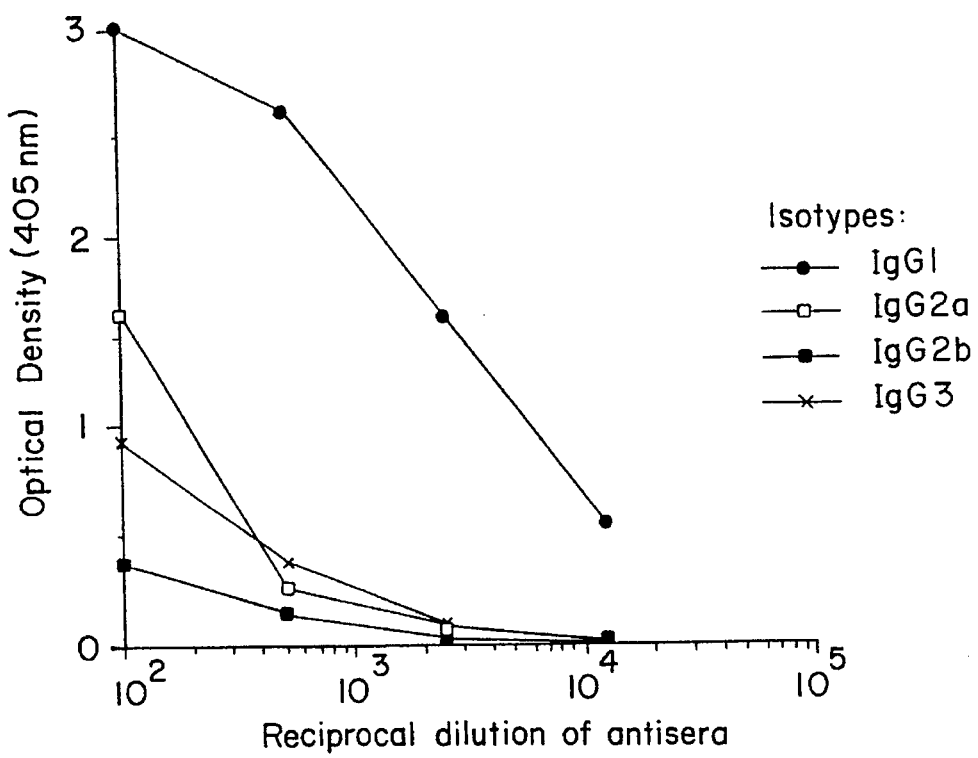
FIG. 5 is a graph showing IgG subclass responses to i.p. inoculated B1M-P3C/liposome. Plates coated with B1 antigen and affinity purified alkaline phosphatase-conjugated antibodies directed against specific IgG subclasses were used.

Since MAP-PLs were developed as a simple replacement of P3C, a lipoMAP model containing three palmitoyl lysine substitutions, B2SM-PL3, a MAP containing four B2 peptides and three palmitoyl lysines on a symmetrical core matrix (FIG. 5C) was tested as a prototype. The humoral response elicited by B2SM-PL3 in mice was analyzed by ELISA. Immunization with B2SM-PL3 in liposomes (B2SM-PL3/lip) elicited antibody response, while B2SM-PL3 alone was not immunogenic (FIG. 5). Furthermore, the response of PL3 was specific, since the same construct with palmitic acids conjugated on the serine side chains such as B2SM-PS3 (FIG. 5A) elicited significantly lower titers than B2SM-PL3 (FIG. 5).

An important question was whether the lipid side chains served solely same as a depot and required a lipid matrix for its correct presentation. The immunogenicity of B2SM-PL3 was then compared in different aqueous and oil-based formulations. In PBS or alum, no significant antibody response was obtained. Only in oil-emulsion or in liposome, did B2SM-PL3 produce significant antibody response (Table 3).

Effect of the linker

Figure 4B:
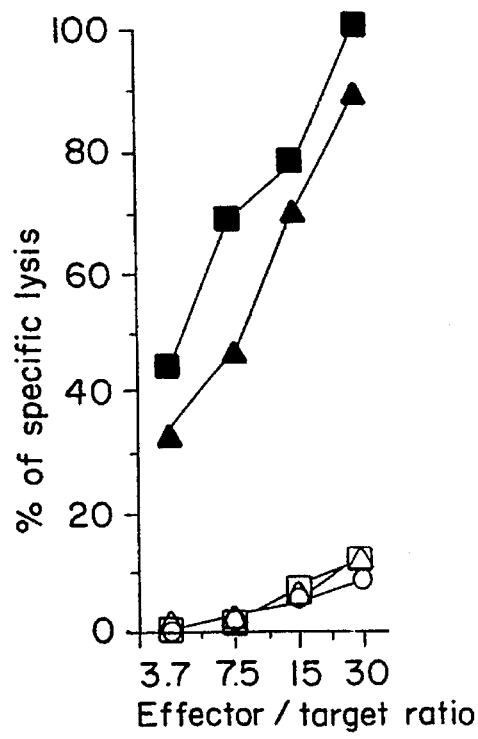

A hydrophilic Ser-Ser linker (18) was inserted between the amino antigen-core matrix and carboxyl lipophilic palmitoyl lysines. Such a linker could exert conformational influence on the overall presentation of our models. To test its conformational influence of MAP-PLs, we compared the linker L-Ser-L-Ser with L-Ser-D-Ser in the B2SM-PL3 and B2SM-D-PL3 models, respectively (FIG. 4B).

With L-Ser-L-Ser as the linker, we envisioned that this linker would allow the antigens to be extruded from the lipid matrix. However, L-Ser-D-Ser imparts a reverse turn to the conjugate and we envisioned such a turn might cause the lipid portion containing the palmitoyl lysines to fold back to the antigen-core matrix, leading to a completely different presentation of antigens in the liposomal matrix. Indeed, B2SM-PL3 in liposomes was immunogenic, while B2SM-D-PL3 which contained the L-Ser-D-Ser linker was weakly immunogenic after three immunizations in mice (FIG. 5).

Effect of numbers of palmitoyl side chain

The immunological responses of B2M-PL3 containing three palmitoyl lysines was in general not as good as B2M-P3C containing three palmitic acids on a cysteine.

However, an inherent advantage to the design of our lipoMAP models was the flexibility to incorporate different numbers of lipid palmitoyl side chains as palmitoyl lysines. To investigate the effect of an optimal number of lipid side chains on immunogenicity, we prepared five models of B2SM containing 0 to 4 palmitoyl lysines, B2SM, B2SM-PL1, B2SM-PL2, B2SM-PL3 and B2SM-PL4 (FIG. 4C).

B2SM-PLs were used to immunize mice alone or incorporated in liposomes. Three of the five models containing 0, 1 and 4 palmitoyl lysines, B2SM, B2SM-PL1 and B2SM-PL4, showed no or very low responses after four immunizations. In the presence of liposomes, virtually no incorporation was observed in the case of B2SM without PL. We found that B2SM-PL1 with a single lipid anchor was very poorly incorporated in the liposomes, and it was very difficult to reach a final concentration of 50 μg of peptide bound to liposomes needed for the immunization. The mice were therefore immunized with B2SM-PL2 (two palmitoyl lysines), B2SM-PL3 (three palmitoyl lysines) and B2SM-PL4 (four palmitoyl lysines) in liposomes or as free constructs, while B2SM (without palmitoyl lysine) and B2SM-PL1 (one palmitoyl lysine) were immunized only as free constructs. The best response was obtained from B2SM-PL2/liposomes. As determined by ELISA against the gp120 peptide (FIG. 6A) and the native protein (FIG. 6B), B2SM-PL2 elicited higher titers than B2SM-PL3. B2SM-PL4 was not immunogenic. No antibody response was detected in the mice immunized with the same concentrations using the free B2SM-PLs.

Induction of cytotoxic T lymphocytes (CTLs)

Figure 7:
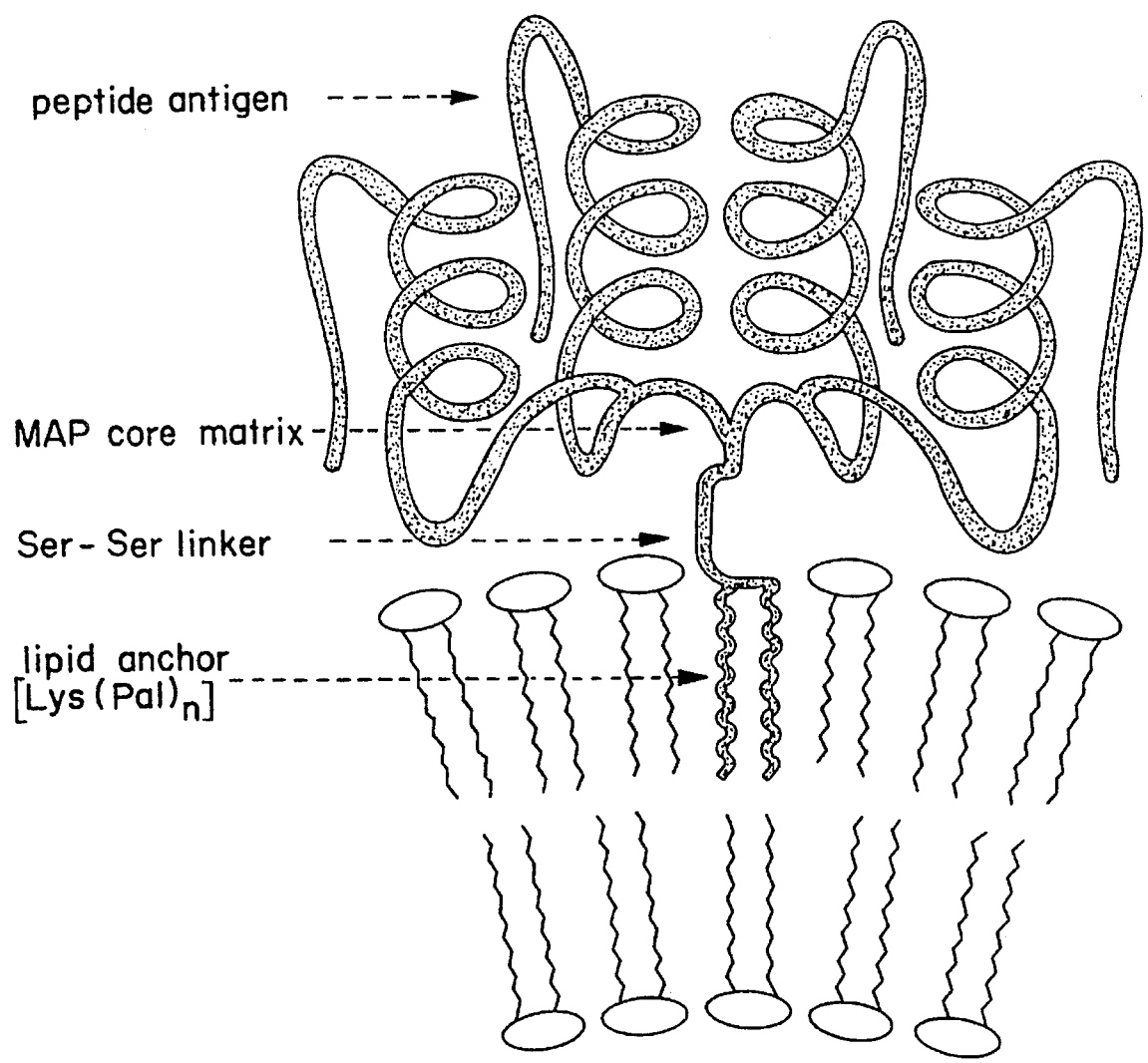
FIG. 7 depicts the schematic structure of a lipoMAP in a lipid matrix.

We then turned our attention to the induction of CTLs which is an important contributor to the immunity against vital infections. Recently, several groups have demonstrated in vivo CTLs priming with peptides or soluble proteins. A common feature in these preparations was the presence of lipophilic moieties attached to peptides (14) or the use of hydrophobic adjuvants, such as Freund's adjuvant or ISCOMs (9,33,28). To assess the induction of CTL response after immunization in our lipoMAP system, spleen cells of the immunized mice were tested for their ability to lyse P815 syngeneic target cells sensitized with B2M peptide. Induction of CTL response, following immunization with the MAP-PL system, was analyzed in BALB/c mice (FIG. 7). Strong cytolytic activity was found in the spleen of the animals immunized with B2SM-PL2 free or in liposomes, indicating that immunodominant cytotoxic epitopes can be coupled to the palmitoyl lysines to raise CTLs in vivo.

Comparison with B2M-P3C

Figure 8:
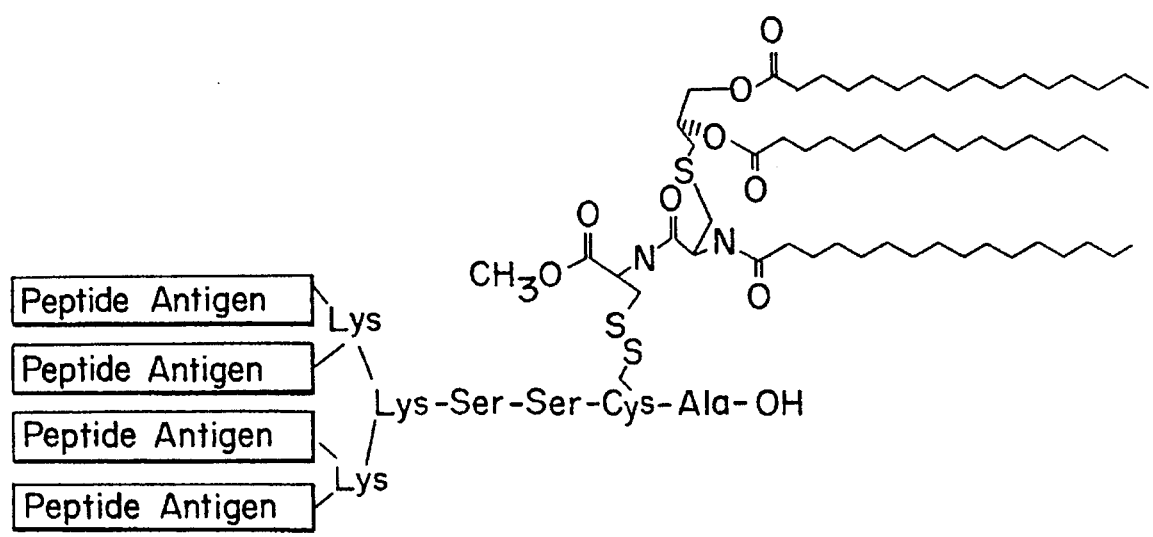
FIG. 8 depicts the schematic representation of tripalmitoyl cysteine conjugate of MAP bearing B2 peptides (B2M-P3C) with a disulfide linkage.
Figure 9A:
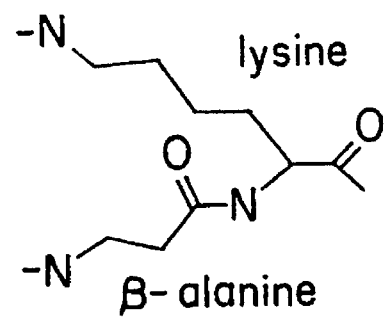
FIG. 9 schematically depicts structural formulas illustrating (A) β-alanyl-lysine; (B) Asymmetrical MAP core (M) and (C) symmetrical MAP core (SM).
Figure 9B:
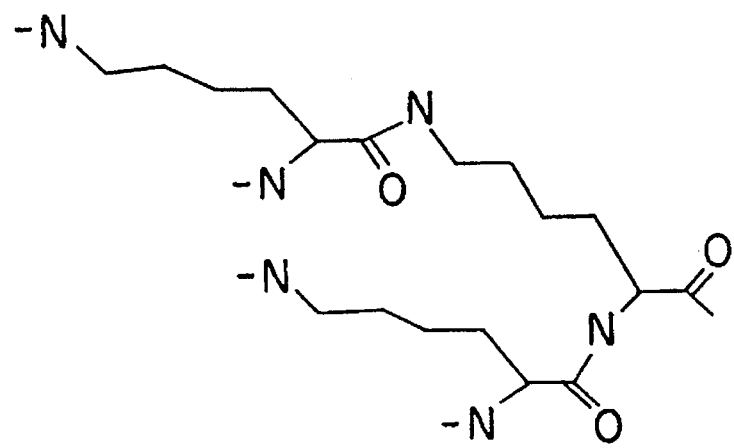
Figure 9C:
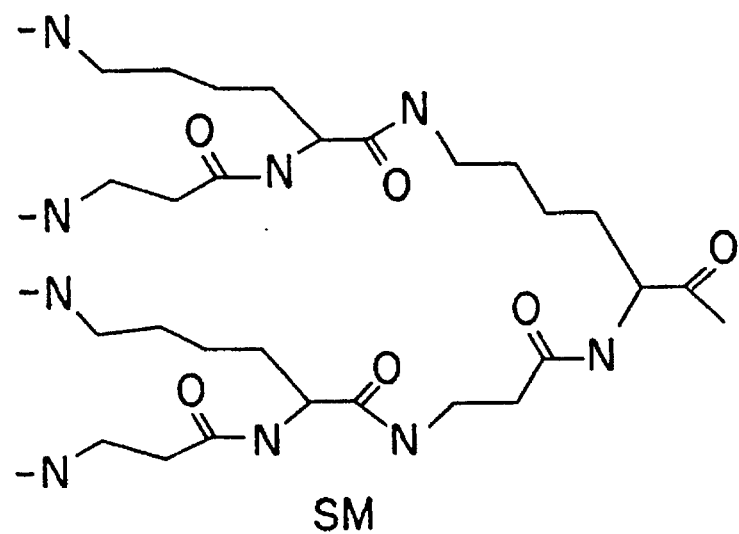

Previously, we have synthesized B2M-P3C, in which P3C was conjugated to the side chain of lysine at the carboxyl terrains, and found that it elicited both humoral and CTLs when incorporated in liposomes (34–36). However, such synthesis of B2M-PC3 using the linkage to the side chain of lysine lacked flexibility. We therefore developed a modular approach (FIG. 8) to the synthesis of B2M-P3C using the thiol side chain of cysteine. It was synthesized by conjugating B2M while it was still attached to the resin to P3C by a disulfide linkage in the solid phase (FIG. 9). The MAP containing a cysteinyl residue at the carboxyl terminus and was then conjugated to a Cys-P3C containing a thiopyridine residue. The advantage of conjugating in the solid phase was that all side products and excess reagents could be removed by washings. The yield of the reaction was 33–54%. However, those B2SM lacking P3C were removed during either the gel permeation chromatography or the incorporation to liposomes. The immunological characteristics of the modular B2M-P3C was compared with those of the new model of B2SM-PL2 and B2SM-PL3. The results are shown in Table 3, below.

TABLE 3

| Comparison of B2SM – PL3 and B2M – P3C | | | |
|---|---|---|---|
| | Titers (10³) | | |
| | B2SM – PL2 | B2SM – PL3 | B2M – P3C |
| PBS | <0.1 | 0.1 | 2 |
| Alum | ND | <0.1 | 40 |
| Oil emulsion | ND | 20 | 2.2 |
| Liposome | 2.0 | 1.7 | 1 |

DISCUSSION

The task of transforming a synthetic peptide antigen into a self-sufficient immunogen capable of eliciting both humoral and cell-mediate responses is challenging. Our results show that the new lipoMAP system with appending, dendritic PLs in a lipid matrix such as liposomes may provide a useful solution. The new system may also be used to further our understanding of immunogenicity and the roles played by the adjuvants.

Adjuvants are known to induce nonspecific B or T-cell proliferations by the induction of cytokines (37). They may also provide a depot for the slow release of the peptide antigens (38). The lipid chains on the lipoMAP appear to provide one or more of these roles. However, it remains to be determined whether the PLs in our lipoMAP play a role to induce cytokines. Our preliminary results have shown that MAP-PLs are not B-cell mitogens (data not shown) and differ from P3C in this aspect.

The advantages of a built-in adjuvant on a peptide antigen have been shown by Chedid and his co-workers (39–41) using derivatives of the muramyl dipeptide, a component of the Freund's adjuvant. Lipid moleties have been used as covalent attachment to the amino terminus, mainly for the purpose of increasing the ability of the peptide antigen to serve as a depot (42–43, 48). We have found that adding lipid moiety to the antigens often alters their immunogencity and have approached this problem in a systematic manner in the design of the lipoMAP system. First, we examine the role of a more flexible core matrix containing a β-alanyl lysine as a building unit which will provide less steric crowding than that using lysine alone. However, the difference of the conventional asymmetric or the new, symmetrical core matrix to improve the presentation of epitope peptide and hence to enhance the antibody response does not appear to be an important factor. We have found that there is essentially no difference in immune response using either core matrix in our model with three PLs (43).

The hydrophilic linker Ser-Ser appears to be important since the use of the Ser-D-Ser linker which orients the lipid portions of the compound differently did not provide the desired immunogenicity. The role of lipid as depot appears to be important since B2SM-PL3 in alum or PBS alone did not result in any significant immunological response. Only those B2SM-PL3 in liposomes (34–35) or in oil-emulsion (36) induce significant antibody response.

We next tested the number of lipid side chains. The optimal number appears to be two. This structural similarity is important for the incorporation and rigid orientation of MAP-PLs on liposomes. The low response of B2SM-PL1 may due to its inability to anchor in liposomes while B2SM-PL3 and B2SM-PL4 have lipid tails crossing each other as shown by molecular simulation. The stereospecific requirements of lipid attachments in Lipid A have been clearly shown by Shiba and his coworkers who have found that altering the number or chirality of the lipid side chains of Lipid A leads to less potent molecules. Similarly, Jung and his coworkers have shown that the chirality (and the orientation) of the palmitoyl side chains of P3C is important for mitogenicity. These results imply that the design of lipoMAP may require to take into consideration the specific conformation of lipid side chains in addition to the presenting peptide antigens on the surfaces of liposomes.

Finally, we have also focused our design on the ability of the peptide antigen to elicit CTLs. We have found that the attachment of PLs with or without the aid of liposomes can induce CTLs capable of killing syngeneic cells expressing gp120 on their cell surfaces (37,45–47). These results show that the processing of B- and T-cell antigens have different requirements. More importantly, it shows the versatility of lipoMAP to elicit both humoral and cell-mediated responses. The simplicity in the design of the lipoMAP and its versatility may be a useful tool for many mechanistic investigations.

The following is a listing of certain of the publications referred to in abbreviated fashion in the foregoing specification, with numbers corresponding to those appearing hereinabove.

1. Grey, H. M. & Chesnut, R. (1985) *Immunol. Today* 6: 101–106.
2. Townsend, A. R., Rothbard, M. J., Gotch, F. M., Bahadur, G., Wraith, D. & McMichael, A. J. (1986) *Cell* 44: 959–968.
3. Unanue, E. R. & Allen, P. M. (1987) *Science* 236: 551–557.
4. Robey, W., Arthur, L., Matthews, T., Langlois, A., Copeland, T., Lerche, N., Oroszlan, S., Bolognesi, D., Gilden, R. & Fischinger, P. (1986) *Proc. Natl. Acad. Sci. USA* 83: 7023–7027.
5. Javaherian, K., Langlois, A., McDanal, C., Ross, K., Eckler, L., Jellis, C., Profy, A., Rusehe, J., Bolognesi, D., Putney, S. & Matthews, T. (1989) *Proc. Natl. Acad. Sci. USA* 86: 6768–6772.
6. Takahashi, H., Merli, S., Putney, S. D., Houghten, R., Moss, R., Germain, R. N. & Berzofsky, J. A. (1989) *Science* 246: 118–121.
7. Lerner, R. A. (1982) *Nature* 299: 592–596.
8. DiMarchi, R., Brooke, G., Gale, C., Cracknell, V., Doel, T. & Mowat, N. (1986) *Science* 232: 639–641.
9. Morein, B. (1988) *Nature* (London) 322: 287–288.
10. Alring, C. R. (1987) *Nature* (London) 330: 189–190.
11. Warren, H. S. & Chedid, L. A. (1988) *CRC Critical Reviews in Immunology* 8: 83–101.
12. Tam, J. P. (1988) *Proc. Natl. Acad. Sci. USA* 85: 5409–5413.
13. Posnett, D. N., McGrath, H. & Tam, J. P. (1988) *J. Biol. Chem.* 263: 1719–1725.
14. Deres, K., Schild, H., Wiesmuller, K-H., Jung, G. & Rammensee, H. (1989) *Nature (London)* 342: 561–564.
15. Nardelli, B., Lu, Y. A., Defoort-Delpierre, C., Shiu, D. R., Profy, A. T. & Tam, J. P. (1992) *J. Immunol.* in press.
16. Merrifield, R. B. (1963) *J. Am. Chem. Soc.* 85: 2149–2154.
17. Wang, S. S. (1975) *J. Org. Chem.* 40: 1235–1239.
18. Wiesmuller, K. H., Besslet, W. G. & Jung, G. (1983) *Hoppe-Seyler's Z. Physsiol. Chem.* 364: 593–606.
19. Sarin, V. K., Kent, S. B. H., Tam, J. P. & Merrifield, R. B. (1981) *Anal. Biochem.* 117: 147–157
20. Gregoriadis, G., Leathwood, P. D. & Ryman, B. E. (1971) *Febs Letters* 14(2): 95–99.
21. Ho, D. D., Sarngadharan, M. G., Martin, S. H., Schooley, R. T., Rota, T. R., Kennedy, R. C., Chanh, T. C. Y Sato, V. L. (1987) *J. Virol.* 61: 2014–2038.
22. Atherton, E., Gait, M. J., Sheppard, R. C., & William, B. J. (1979) *Bioorg. Chem.* 8: 351–361.
23. Lu, Y. A., Clavijo, P., Galantino, M., Shen, Z. Y., Liu, W. & Tam, J. P. (1991) *Molecular Immunol.* 28: 623–630.
24. Nardelli, B., Defoort, J. P., Huang, W. & Tam, J. P. (1992) *AIDS Res. & Human Retroviruses* in press.
25. Orentas, R. J., Hildreth, J. E. K., Obah, E., Polydefkis, M., Smith, G. E., Clements, M. L. & Siliciano, R. F. (1990) *Science* 248: 1234–1237.
26. Hu, S. L., Kosowski, S. G. & Dalymple, J. (1986) *Nature (London)* 320: 537–539.
27. Clarke, B. E., Newton, S. E., Carroll, A. R., Francis, M. J., Appleyard, G., Syred, A. D., Highfield, P. E., Rowlands, D. J. & Brown, F. (1987) *Nature (London)* 330: 381–383.
28. Takahashi, H., Takashita, T., Morein, B., Putney, S., Germain, N. & Berzofsky, J. A. (1990) *Nature* 344: 873–875.
29. Lowell, G. H., Ballou, W. R., Smith, L. F., Wirtz, R. A., Zollinger, W. D. & Hockmeyer, W. T. (1988) *Science* 240: 800–802.
30. Defoort, J. P., Nardelli, B., Huang, W., Shiu, D. R., Ho, D., & Tam, J. P. (1992) *Proc. Natl. Acad. Sci. USA* 89: 3879–3883.
31. Brenan, M. (1983) *Immunol. Today* 4: 319–320.
32. Defoort, J.-P., Nardelli, B., Huang, W., & Tam, J. P. (1992) *Int. J. Peptide Protein Res.* 40: 214–221.
33. Schultz, Zinkernagel, R. M., & Hergartner, H. (1991) *Proc. Natl. Acad. Sci. USA* 88: 991.
34. Gregoriadis, G. (1990) *Immunol. Today* 11 (3): 89–97.
35. Allison, A. C., & Gregoriadis, G. (1974) *Nature (London)* 252: 252.
36. Pyle, S. W., Morein, B., Bess, J. W., Jr., Akerblom, L., Nara, P. L., Nigida, S. M., Jr., Lerche, N. W., Robey, W. G., Fischinger, P. J., Arthur, L. O. (1989) *Vaccine* 7: 465–473.
37. Vitetta, E. S., Bossie, A., Fernandez-Botran, R., Myers, C. D., Oliver, K. G., Saners, V. M., Stevens, T. L. (1987). *Immunol. Rev.* 99: 193–239.
38. Edelman, R. (1980) *Rev. Infect. Dis.* 2: 370–383.
39. Audibert, F., Leclerc, C., Chexlid, L. (1985) Muramyl peptide as immunopharmacological response modifiers. In Torrence, P. F., ed. *Biological Response Modifiers: New Approaches to Disease Intervention.* New York: Academic Press, 207–327.
40. Ho, R. J. Y., Burke, R. I., Ott, G., Merigan, T. C. (1989) *J. Virol.* 63(7): 2951–2958.
41. Iido, J., Saikii I., Ishira, C., Azuma, I. (1989) *Vaccine* 7: 225–228.
42. Kenney, J. S., Hughes, B. W., Masad, M. P., Allison, A. C. (1989) *J. Immunol. Meth.* 121: 157–166.
43. Huang, W. In Peptides: Chemistry and Biology (Proceedings of the 12th American Peptide Symposium).
44. Finberg, R., Mescher, M., Burakoff, S. J. (1978) The induction of virus-specific cytotoxic T lymphocytes with solubilized viral and membrane proteins. *J. Exp. Med.* 148: 1620–1627.
45. Abbas, A. K. (1987) Cellular interactions in the immune response: The roles of B lymphocytes and interleukin-4. *Am. J. Pathol.* 129: 25–33.
46. Buus, S., Sette, A., Grey, H. M. (1987) The interaction between protein-derived immunogenic peptides and Ia. *Immunol. Rev.* 98: 115–141.
47. Babbitt, B. P., Allen, P. M., Matsueda, G., Haber E., Unanue, E. R. (1985). Binding of immunogenic peptides to Ia histocompatibility molecules. *Nature* 317: 359–361.

48. Byrnestad, K., Babbitt, B., Huang, L., Rouse, B. T. (1990) Influence of peptide acylation, liposome incorporation, and synthetic immunomodulators on the immunogenicity for subunit vaccines. *J. Virol.* 64(2): 680–685.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A multiple antigen peptide system comprising a dendritic core to which are covalently attached at least one peptide and a lipophilic membrane anchoring moiety, wherein said multiple antigen peptide system exhibits adjuvant properties and when injected into a mammal, is capable of eliciting a full immune response provided by both humoral and cell mediated immunities including a cytotoxic T lymphocyte immune response.

2. The multiple antigen peptide system of claim 1 wherein said lipophilic membrane anchoring moiety comprises a constituent selected from the group consisting of a lipoamino acid, a liposome, a saponin derivative alone or in admixture with cholesterol, and a suitable surfactant material.

3. The multiple antigen peptide system of claim 2, wherein said lipophilic membrane anchoring moiety comprises a lipoamino acid.

4. The multiple antigen peptide system of claim 1 wherein said dendritic core comprises a bifunctional unit.

5. The multiple antigen peptide system of claim 1 further comprising a covalently attached T cell epitope.

6. The multiple antigen peptide system of claim 3 wherein said lipoamino acid is derived from amino acids selected from the group consisting of cysteine, lysine, serine and mixtures thereof.

7. The multiple antigen peptide system of claim 6 wherein said lipophilic membrane anchoring moiety comprises tripalmitoyl-S-glycerylcysteine.

8. The multiple antigen peptide system of claim 6 wherein said lipophilic membrane anchoring moiety comprises dipalmitoyl-S-glycerylcysteine.

9. The multiple antigen peptide system of claim 6 wherein said lipophilic membrane anchoring moiety comprises palmitoyl lysine.

10. The multiple antigen peptide system of claim 3 wherein said lipoamino acid is covalently attached through a peptide bond to an amino acid polymer comprising a peptide.

11. The multiple antigen peptide system of claim 10 wherein said peptide is a lipopeptide.

12. The multiple antigen peptide system of claim 5 wherein said T cell epitope is covalently linked to said peptide.

13. The multiple antigen peptide system of claim 12 wherein said T cell epitope is covalently linked in tandem to said peptide.

14. The multiple antigen peptide system of claim 5 wherein said T cell epitope is at least seven amino acids long.

15. The multiple antigen peptide system of claim 5 wherein the T cell epitope is a cytotoxic T cell epitope.

16. The multiple antigen peptide system of claim 5 wherein the T cell epitope is a helper T cell epitope.

17. The multiple antigen peptide system of claim 5 wherein the T cell epitope is derived from an HIV-1 protein.

18. The multiple antigen peptide system of claim 17 wherein the HIV-1 protein is the HIV-1 envelope glycoprotein.

19. The multiple antigen peptide system of claim 1 wherein said system is encapsulated within a liposome.

20. The multiple antigen peptide system of claim 1 wherein said dendritic core comprises lysine.

21. The multiple antigen peptide system of claim 1 wherein said peptide is between 10 and 40 amino acids long.

22. The multiple antigen peptide system of claim 5 further comprising a B cell epitope.

23. The multiple antigen peptide system of claim 22 wherein the B cell epitope and the T cell epitope are linked on the same functional group of the dendritic core.

24. The multiple antigen peptide system of claim 4 wherein said dendritic core is tetravalent.

25. The multiple antigen peptide system of claim 2 wherein said suitable surfactant material comprises a mixture of long chain polyoxyethylenes and polyoxypropylenes.

26. The multiple antigen peptide system of claim 4 wherein the bifunctional unit comprises an amino acid selected from the group consisting of cysteine, lysine, aspartic acid, glutamic acid, and ornithine.

27. The multiple antigen peptide system of claim 26 comprising eight free functional groups in the dendritic core and eight peptides, wherein each of the eight peptides is attached to each of the eight free functional groups, thereby forming an octavalent multiple peptide antigen.

28. The multiple antigen peptide system of claim 27 further comprising eight covalently attached T cell epitopes.

29. The multiple antigen peptide system of claim 28 wherein the T cell epitopes are derived from an HIV-1 protein.

30. The multiple antigen peptide system of claim 28 wherein the lipophilic membrane anchoring moiety comprises a constituent selected from the group consisting of a lipoamino acid, a liposome, a saponin derivative alone or in admixture with cholesterol, and a suitable surfactant material.

31. The multiple antigen peptide system of claim 30 wherein the lipophilic membrane anchoring moiety is a lipoamino acid derived from an amino acid selected from the group consisting of cysteine, lysine, serine and mixtures thereof.

32. The multiple antigen peptide system of claim 30 wherein the lipophilic membrane anchoring moiety is a lipoamino acid selected from the group consisting of tripahnitoyl-S-glycerylcysteine, dipalmitoyl-S-glycerylcysteine, and palmitoyl lysine.

33. A method for generating antibodies in a mammal, said method comprising administering to said mammal an antibody-generating amount of the multiple antigen peptide system of claim 1.

34. A method for generating antibodies in a mammal said method comprising administering to said mammal an antibody-generating amount of the multiple antigen peptide system of claim 32.

35. A method for generating antibodies in a mammal said method comprising administering to said mammal an antibody-generating amount of the multiple antigen peptide system of claim 23.

36. A method for generating antibodies in a mammal said method comprising administering to said mammal an antibody-generating amount of the multiple antigen peptide system of claim 5.

* * * * *